(12) United States Patent
Cheng et al.

(10) Patent No.: US 12,274,164 B2
(45) Date of Patent: Apr. 8, 2025

(54) PYRIDINE-CARBONITRILE COMPOUND AND ELECTROLUMINESCENT DEVICE INCLUDING THE SAME

(71) Applicant: National Tsing Hua University, Hsinchu (TW)

(72) Inventors: Chien-Hong Cheng, Hsinchu (TW); Yi-Kuan Chen, Hsinchu (TW); Jayakumar Jayachandran, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 739 days.

(21) Appl. No.: 17/163,573

(22) Filed: Feb. 1, 2021

(65) Prior Publication Data

US 2022/0209129 A1 Jun. 30, 2022

(30) Foreign Application Priority Data

Dec. 18, 2020 (TW) .................................. 109144905

(51) Int. Cl.
*H10K 85/60* (2023.01)
*C07D 213/85* (2006.01)
(Continued)

(52) U.S. Cl.
CPC ......... *H10K 85/654* (2023.02); *C07D 213/85* (2013.01); *C07D 401/10* (2013.01);
(Continued)

(58) Field of Classification Search
CPC ... H10K 85/654; H10K 85/636; C07D 213/85
See application file for complete search history.

(56) References Cited

U.S. PATENT DOCUMENTS 9,893,300 B1 * 2/2018 Cheng .................. C07D 403/04
2015/0001521 A1 * 1/2015 Huang ............... H10K 85/6572
548/266.4
(Continued)

FOREIGN PATENT DOCUMENTS

CN  109535131  3/2019
CN  113105435  7/2021
(Continued)

OTHER PUBLICATIONS

"Office Action of Taiwan Counterpart Application", issued on Jun. 15, 2021, p. 1-p. 5.
(Continued)

*Primary Examiner* — Liam J Heincer
(74) *Attorney, Agent, or Firm* — JCIPRNET

(57) ABSTRACT

Provided are an aromatic compound represented by Chemical Formula 1 and an electroluminescent device including the same. In Chemical Formula 1, $R_1$, $R_2$, $R_3$, $Ar_1$, and $Ar_2$ are the same as described in the detailed description.

[Chemical Formula 1]

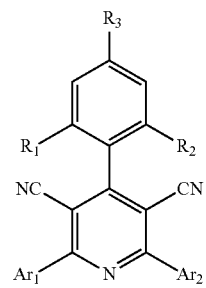

9 Claims, 8 Drawing Sheets

TPAmPPC      TPAPPC      TPAsPPC

HOMO

LUMO

(51) Int. Cl.
  *C07D 401/10* (2006.01)
  *C09K 11/06* (2006.01)
  *H10K 50/11* (2023.01)
  *H10K 101/10* (2023.01)
(52) U.S. Cl.
  CPC ............ *C09K 11/06* (2013.01); *H10K 85/636* (2023.02); *H10K 85/6572* (2023.02); *C09K 2211/1018* (2013.01); *H10K 50/11* (2023.02); *H10K 2101/10* (2023.02)

(56) References Cited

U.S. PATENT DOCUMENTS

2017/0309835 A1\* 10/2017 Kim .................. H10K 85/6574
2019/0296246 A1   9/2019 Hayano et al.

FOREIGN PATENT DOCUMENTS

TW   201721929    6/2017
WO   2016208240   12/2016

OTHER PUBLICATIONS

Jayachandran Jayakumar et al., "Pyridine-Carbonitrile-Carbazole-Based Delayed Fluorescence Materials with Highly Congested Structures and Excellent OLED Performance," ACS Appl. Mater. Interfaces, vol. 11, No. 23, May 15, 2019, pp. 21042-21048.
Hiroki Uoyama et al., "Highly efficient organic light-emitting diodes from delayed fluorescence," Nature, vol. 492, Dec. 12, 2012, pp. 234-238.
Mallesham Godumala et al., "Recent breakthroughs in thermally activated delayed fluorescence organic light emitting diodes containing non-doped emitting layers," Journal of Materials Chemistry C, vol. 7, Issue 8, Jan. 2019, pp. 2172-2198.
Ye Tao et al., "Thermally Activated Delayed Fluorescence Materials Towards the Breakthrough of Organoelectronics," Advanced Materials, vol. 26, Issue 47, Sep. 17, 2014, pp. 7931-7958.
Michael Y. Wong et al., "Purely Organic Thermally Activated Delayed Fluorescence Materials for Organic Light-Emitting Diodes," Advanced Materials, vol. 29, Issue 22, Mar. 3, 2017, pp. 1-54.
Yuchao Liu et al., "All-organic thermally activated delayed fluorescence materials for organic light-emitting diodes," Nature Reviews Materials, vol. 3, Article No. 18020, Apr. 10, 2018, pp. 1-20.
Wei Liu et al., "Novel Carbazol-Pyridine-Carbonitrile Derivative as Excellent Blue Thermally Activated Delayed Fluorescence Emitter for Highly Efficient Organic Light-Emitting Devices," ACS Appl. Mater. Interfaces, vol. 7, No. 34, Aug. 20, 2015, pp. 18930-18936.
Zhanxiang Chen et al., "Emitters with a pyridine-3,5-dicarbonitrile core and short delayed fluorescence lifetimes of about 1.5 μs: orange-red TADF-based OLEDs with very slow efficiency roll-offs at high luminance," Journal of Materials Chemistry C, vol. 6, Issue 24, May 2018, pp. 6543-6548.
Lin Gan et al., "Achieving Efficient Triplet Exciton Utilization with Large ΔEST and Nonobvious Delayed Fluorescence by Adjusting Excited State Energy Levels," J. Phys. Chem. Lett., vol. 9, No. 16, Aug. 1, 2018, pp. 4725-4731.
Zhanxiang Chen et al., "Enhancing Spin—Orbit Coupling by Introducing a Lone Pair Electron with p Orbital Character in a Thermally Activated Delayed Fluorescence Emitter: Photophysics and Devices," J. Phys. Chem. Lett., vol. 10, No. 11, May 6, 2019, pp. 2669-2675.
Jiafang Li et al., "Double-twist pyridine-carbonitrile derivatives yielding excellent thermally activated delayed fluorescence emitters for high-performance OLEDs," Journal of Materials Chemistry C, vol. 8, Issue 2, Nov. 2019, pp. 602-606.
Sheng-Lin Deng et al., "Modifications of Pyridine-3,5-dicarbonitrile Acceptor for Highly Efficient Green-to-Red Organic Light-Emitting Diodes", ACS Applied Materials & Interfaces, Jul. 7, 2023, pp. 33819-33828, vol. 15, No. 28.
Yi-Kuan Chen et al., "Increase the molecular length and donor strength to boost horizontal dipole orientation for high-efficiency OLEDs", Journal of Materials Chemistry C, May 26, 2022, pp. 9241-9248, vol. 10, No. 24.
Yi-Kuan Chen et al., "Triarylamine-Pyridine-Carbonitriles for Organic Light-Emitting Devices with EQE Nearly 40%", Advanced Materials, Dec. 31, 2021, pp. 2008032(1-8).
He Liu et al., "A simple strategy to achieve efficient thermally activated delayed fluorescent emitters via enhancing electron donating ability of donors", Dyes and Pigments, May 11, 2020, pp. 1-7, vol. 180, No. 108521.
Xudong Cao et al., "CN-Containing donor-acceptor-type small-molecule materials for thermally activated delayed fluorescence OLEDs", Journal of Materials Chemistry C, Jul. 11, 2017, pp. 7699-7714, vol. 5.
"Office Action of China Counterpart Application", issued on Nov. 16, 2023, p. 1-p. 9.

\* cited by examiner

PYRIDINE-CARBONITRILE COMPOUND AND ELECTROLUMINESCENT DEVICE INCLUDING THE SAME

CROSS-REFERENCE TO RELATED APPLICATION

This application claims the priority benefit of Taiwanese application no. 109144905, filed on Dec. 18, 2020. The entirety of the above-mentioned patent application is hereby incorporated by reference herein and made a part of this specification.

BACKGROUND

Technical Field

The disclosure relates to a compound, and particularly relates to a pyridine-carbonitrile compound and an electroluminescent device including the same.

Related Art

Conventionally, a fluorescent material may serve as a luminous body in an organic light-emitting diode (OLED) element. Due to the spin selection rule, a use ratio of excitons is low, resulting in insufficient luminous efficiency of the light-emitting element. In current phosphorescent materials, by introduction of a precious metal, spin-orbital coupling (SOC) is enhanced, thereby improving the luminous efficiency of the light-emitting element. However, since the introduced precious metal (such as iridium and platinum) is costly, the manufacturing cost of the light-emitting element is increased, which is less favorable for commercial application.

The development of thermally activated delayed fluorescent (TADF) materials has recently become a hot research field. A TADF material has high luminous efficiency and low cost. To impart TADF characteristics to a light-emitting molecule, a key point is to reduce an energy gap ($\Delta E_{ST}$) between the lowest singlet excited state ($S_1$) and the lowest triplet excited state ($T_1$). When $\Delta E_{ST}$ is sufficiently small, endothermic reverse intersystem crossing (RISC) may be induced by environmental stimuli such as thermal activation. In an electric excitation process, 25% of singlet excitons and 75% of triplet excitons are captured at the same time, thereby achieving 100% internal quantum efficiency.

However, when $\Delta E_{ST}$ is too small, the ability to transition between an excited state and a ground state may be reduced, and the occurrence of non-radiative paths may be increased, thus reducing the photoluminescence quantum yield (PLQY). Therefore, emission characteristics of a material may be determined by the structural design of the light-emitting molecule.

In addition, since a typical TADF material has a relatively long delayed fluorescence lifetime of about tens to hundreds of microseconds (μs), and excitons at high energy are prone to quenching, efficiency performance and operational stability of the light-emitting element under high luminance conditions are limited. Thus, the reliability and lifetime of the typical TADF material applied in an electroluminescent device are reduced.

SUMMARY

The disclosure provides a pyridine-carbonitrile compound capable of realizing an electroluminescent element with high luminous efficiency.

The disclosure provides a pyridine-carbonitrile compound represented by Chemical Formula 1:

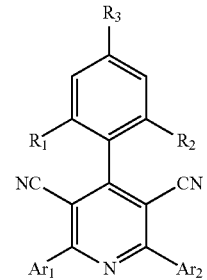

[Chemical Formula 1]

In Chemical Formula 1, $Ar_1$ and $Ar_2$ may be the same or different and are each independently a substituted or unsubstituted aryl group, or a substituted or unsubstituted heteroaryl group; $R_1$ and $R_2$ may be the same or different and are each independently a substituted or unsubstituted alkyl group; and $R_3$ is a nitrogen-containing group.

In one embodiment of the disclosure, $R_3$ is one selected from the following structures:

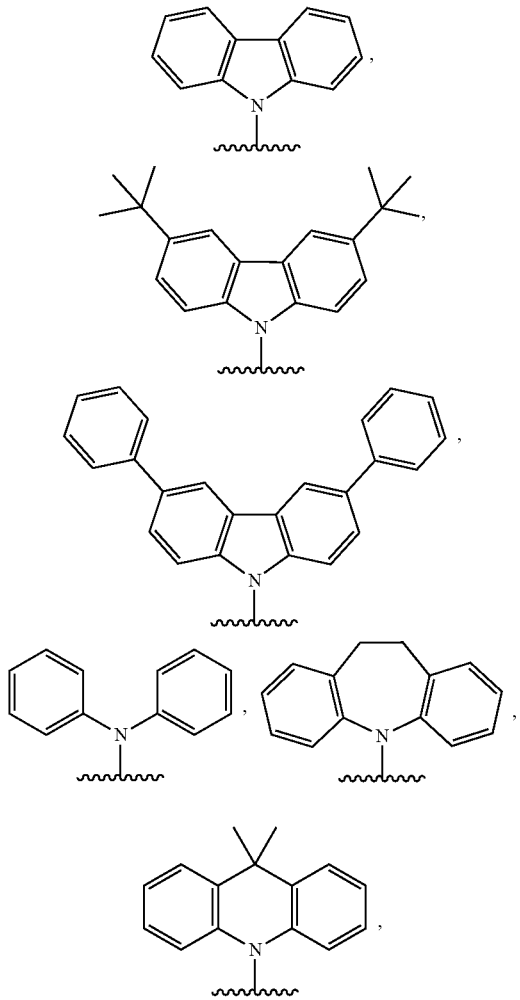

-continued

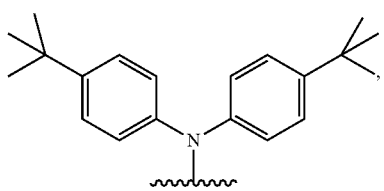

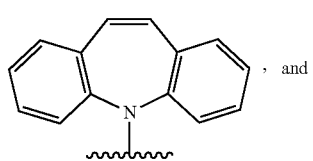, and

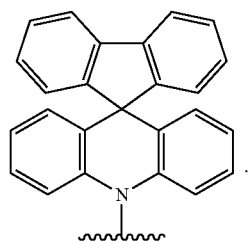.

In one embodiment of the disclosure, $Ar_1$ and $Ar_2$ are each independently one selected from the following structures:

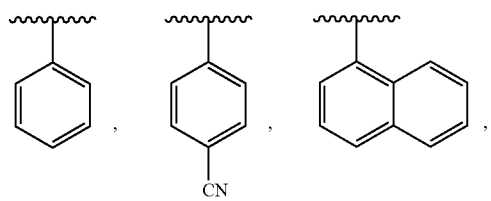

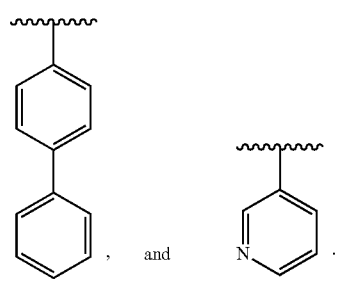, and .

In one embodiment of the disclosure, $R_1$ and $R_2$ are each independently a methyl group, an ethyl group or a propyl group.

In one embodiment of the disclosure, the pyridine-carbonitrile compound is represented by one of the following structural formulas:

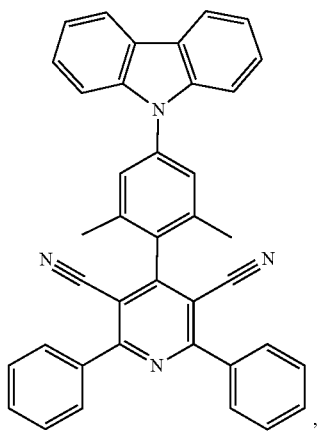,

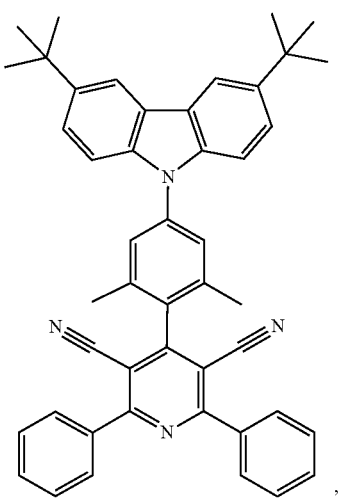,

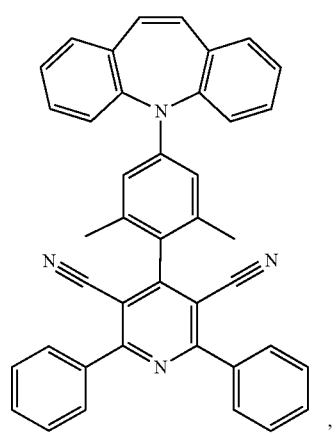,

5
-continued
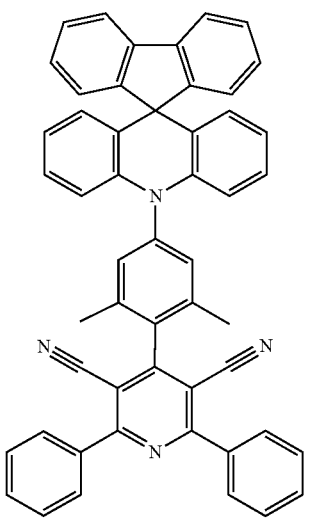 [SMILES: Cc1cc(N2c3ccccc3C3(c4ccccc4-c4ccccc43)c3ccccc32)cc(C)c1-c1c(C#N)c(-c2ccccc2)nc(-c2ccccc2)c1C#N]
,
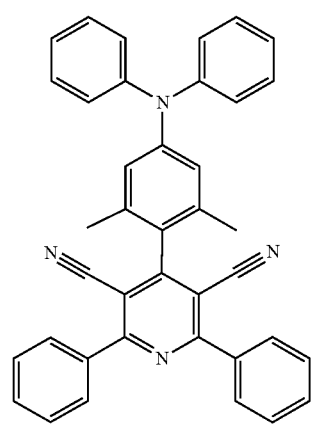 [SMILES: Cc1cc(N(c2ccccc2)c2ccccc2)cc(C)c1-c1c(C#N)c(-c2ccccc2)nc(-c2ccccc2)c1C#N]
,
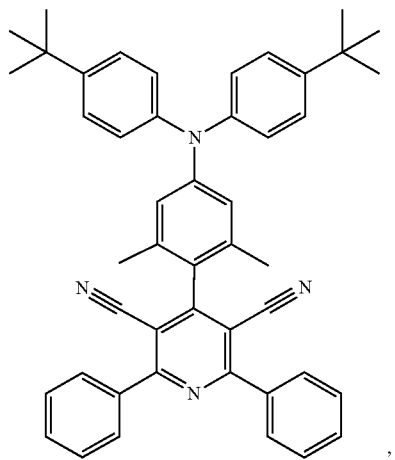
,
6
-continued
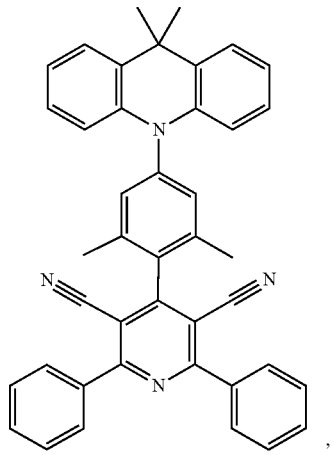
,
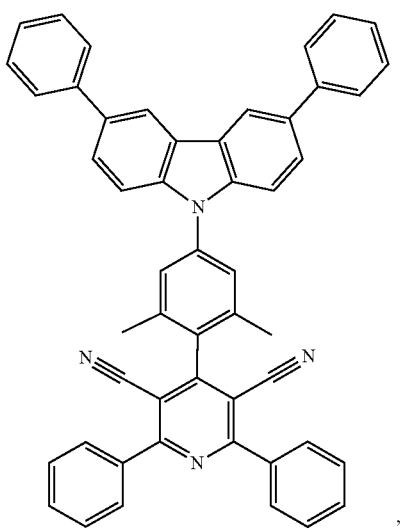
,
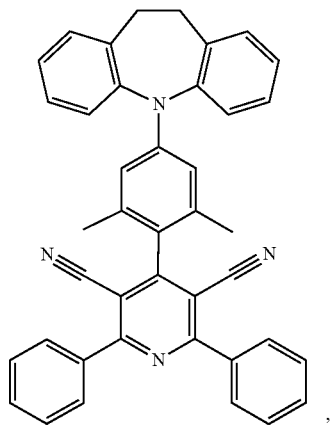
,

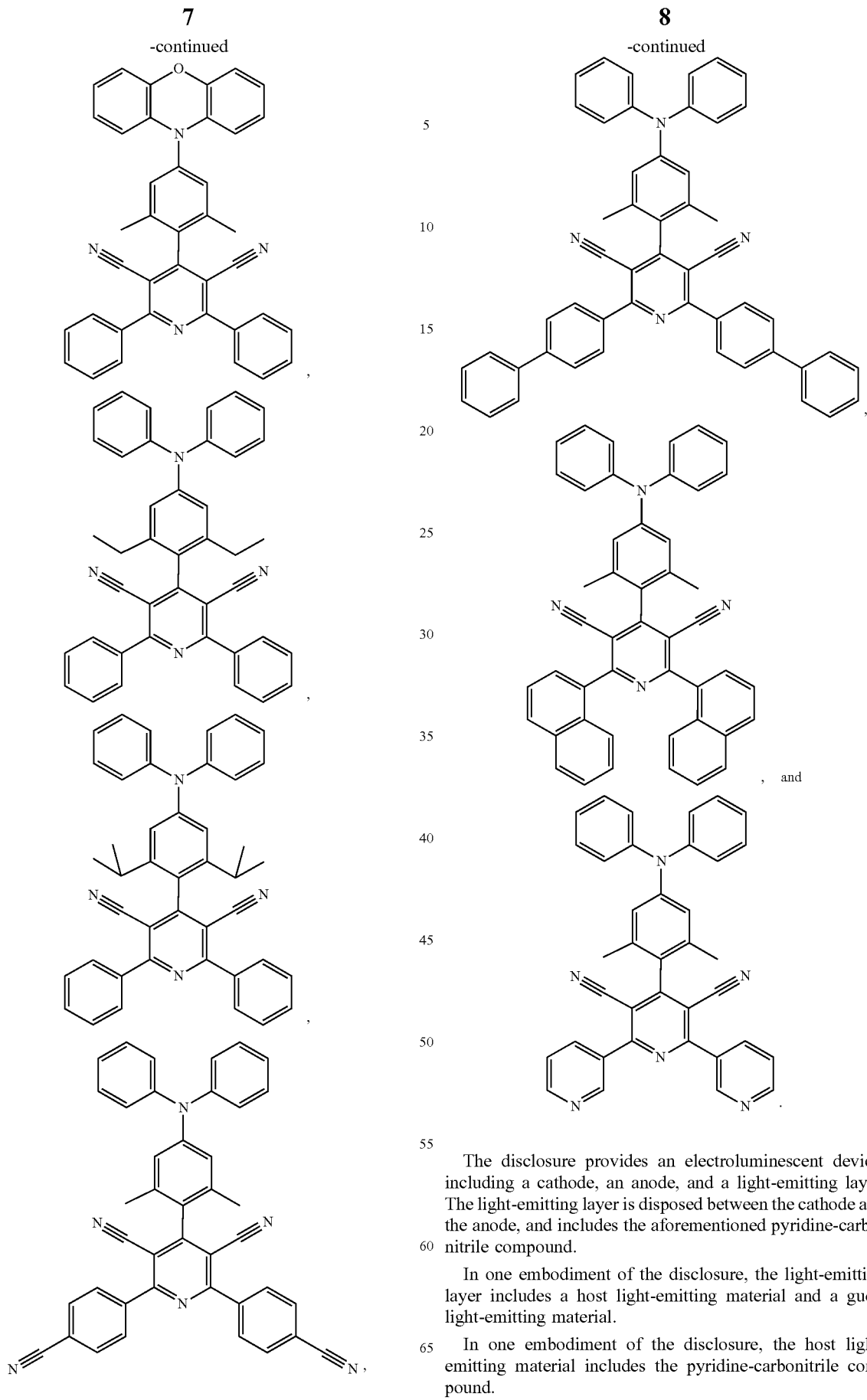

The disclosure provides an electroluminescent device, including a cathode, an anode, and a light-emitting layer. The light-emitting layer is disposed between the cathode and the anode, and includes the aforementioned pyridine-carbonitrile compound.

In one embodiment of the disclosure, the light-emitting layer includes a host light-emitting material and a guest light-emitting material.

In one embodiment of the disclosure, the host light-emitting material includes the pyridine-carbonitrile compound.

In one embodiment of the disclosure, the guest light-emitting material includes the pyridine-carbonitrile compound.

In one embodiment of the disclosure, the electroluminescent device further includes at least one auxiliary layer. The auxiliary layer is selected from the group consisting of a hole injection layer, a hole transport layer, a hole blocking layer, an exciton blocking layer, an electron injection layer, an electron transport layer, and an electron blocking layer.

Based on the above, the pyridine-carbonitrile compound of the present embodiment enables emission of light of different colors and has a high PLQY, excellent thermal stability and TADF characteristics. In the pyridine-carbonitrile compound of the disclosure, by introducing a cyano group into positions 3 and 5 of a pyridyl group, the electron accepting capacity of the pyridyl group is improved. In addition, the pyridine-carbonitrile compound of the disclosure uses pyridine-3,5-dicarbonitrile as an electron withdrawing group to thereby improve the overall charge transfer property of molecules and reduce an electron cloud overlap between the highest occupied molecular orbital (HOMO) and the lowest unoccupied molecular orbital (LUMO), so as to reduce $\Delta E_{ST}$. In this way, TADF characteristics are achieved, and luminous efficiency of an electroluminescent device fabricated using the pyridine-carbonitrile compound can be improved.

In addition, in the pyridine-carbonitrile compound of the present embodiment, by introducing the nitrogen-containing group serving as an electron donor into the para position of a phenyl group serving as a linking group, emission color and photoluminescence quantum yield (PLQY) of the molecules can be controlled. In addition, in the pyridine-carbonitrile compound of the present embodiment, by introducing the alkyl group into the ortho position of the phenyl group serving as the linking group, a steric hindrance effect between the alkyl group and the cyano group increases a dihedral angle between the phenyl group and pyridine-3,5-dicarbonitrile, thereby reducing the electron cloud overlap between the HOMO and the LUMO. In addition, the electroluminescent device of the present embodiment includes the pyridine-carbonitrile compound in the light-emitting layer, and is therefore improved in external quantum efficiency and extended in lifetime.

To make the aforementioned more comprehensible, several embodiments accompanied with drawings are described in detail as follows.

DESCRIPTION OF THE EMBODIMENTS

Figure 1:
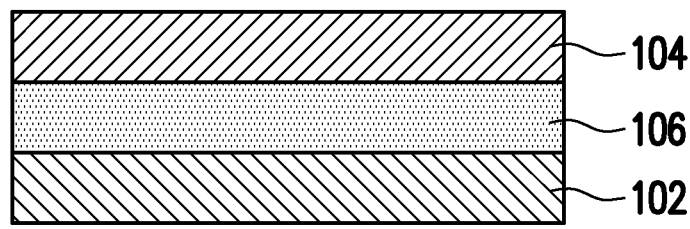
FIG. 1 is a schematic cross-sectional view of an electroluminescent device according to one embodiment of the disclosure.

The technical solutions of the disclosure will be clearly and completely described below with reference to the accompanying drawings. Evidently, the embodiments to be described are some rather than all embodiments of the disclosure. Based on the embodiments of the disclosure, all other embodiments which can be derived by those of ordinary skill in the art from the embodiments and the accompanying drawings shall fall within the protection scope of the disclosure.

In the description of the disclosure, terms such as "first", "second" and "third" are only used for description and should not be understood as indicating or implying relative importance.

The disclosure can be implemented in many different forms and should not be construed as being limited to the embodiments set forth herein. On the contrary, these embodiments are provided so that the disclosure will be thorough and complete, and will fully convey the concept of the disclosure to those of ordinary skill in the art, and the scope of the disclosure should only be limited by what is claimed. In the accompanying drawings, the sizes and relative sizes of layers and regions may be exaggerated for clarity. It should be understood that when an element such as a layer is referred to as being "formed on" or "disposed on" another element, the element may be directly disposed on the another element, or an intervening element may also be present. In contrast, when an element is referred to as being "directly formed on" or "directly disposed on" another element, there is no intervening element.

In the present specification,

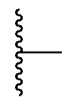

means a portion connected to another substituent.

In the present specification, unless otherwise defined, the term "substituted" refers to substitution with the following groups: halogen, aryl group, hydroxyl group, alkenyl group, $C_1$-$C_{20}$ alkyl group, alkynyl group, cyano group, trifluoromethyl group, alkylamino group, amino group, $C_1$-$C_{20}$ alkoxy group, heteroaryl group, aryl group having a halogen substituent, aralkyl group having a halogen substituent, aryl group having a haloalkyl substituent, aralkyl group having a haloalkyl substituent, $C_1$-$C_{20}$ alkyl group having an aryl substituent, cycloalkyl group, amino group having a $C_1$-$C_{20}$ alkyl substituent, amino group having a haloalkyl substituent, amino group having an aryl substituent, amino group having a heteroaryl substituent, phosphinyloxy group having an aryl substituent, phosphinyloxy group having a $C_1$-$C_{20}$ alkyl substituent, phosphinyloxy group having a haloalkyl substituent, phosphinyloxy group having a halogen substituent, phosphinyloxy group having a heteroaryl substituent, nitro group, carbonyl group, arylcarbonyl group, heteroarylcarbonyl group, or $C_1$-$C_{20}$ alkyl group having a halogen substituent.

Embodiments of the disclosure will be described below in detail. However, these embodiments are exemplary, and the disclosure is not limited thereto.

A pyridine-carbonitrile compound according to one embodiment of the disclosure is represented by the following Chemical Formula 1:

[Chemical Formula 1]

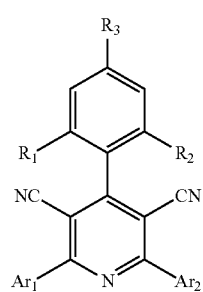

In Chemical Formula 1, $Ar_1$ and $Ar_2$ may be the same or different and are each independently a substituted or unsubstituted aryl group, or a substituted or unsubstituted heteroaryl group; $R_1$ and $R_2$ may be the same or different and are each independently a substituted or unsubstituted alkyl group; and $R_3$ is a nitrogen-containing group.

In one embodiment of the disclosure, $R_3$ is one selected from the following structures:

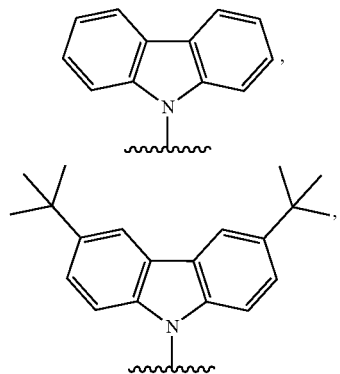

-continued

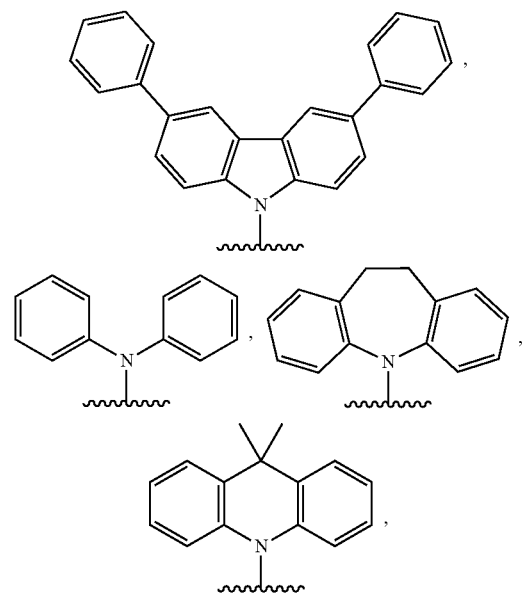

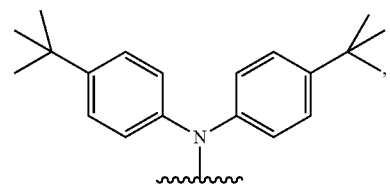

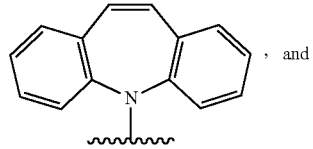

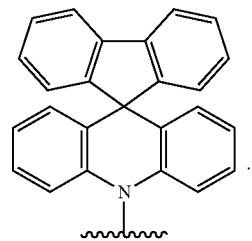, and

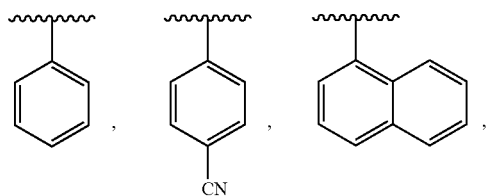

In one embodiment of the disclosure, $Ar_1$ and $Ar_2$ are each independently one selected from the following structures:

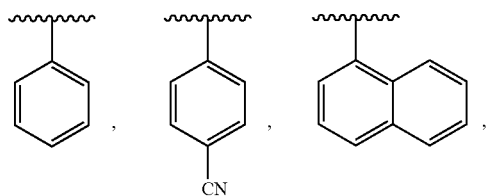

-continued
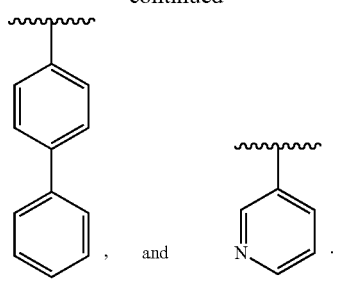, and
In one embodiment of the disclosure, $R_1$ and $R_2$ are each independently a methyl group, an ethyl group or a propyl group.
In one embodiment of the disclosure, the pyridine-carbonitrile compound is represented by one of the following structural formulas:
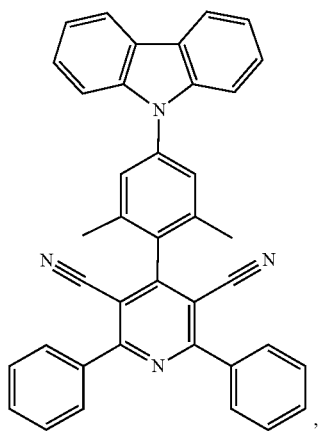,
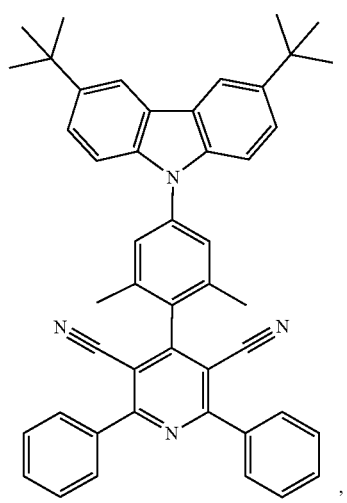,
-continued
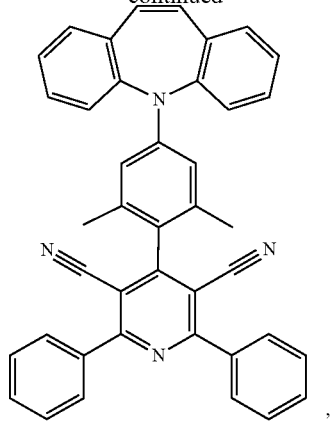,
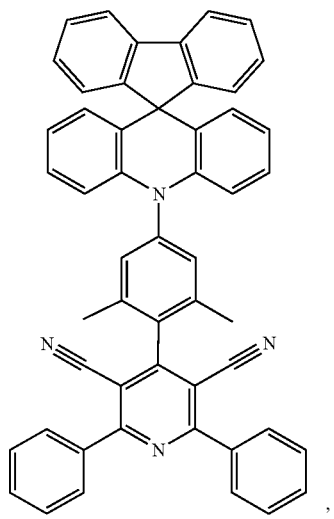,
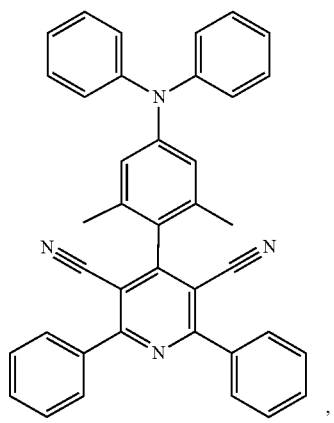, 15
-continued
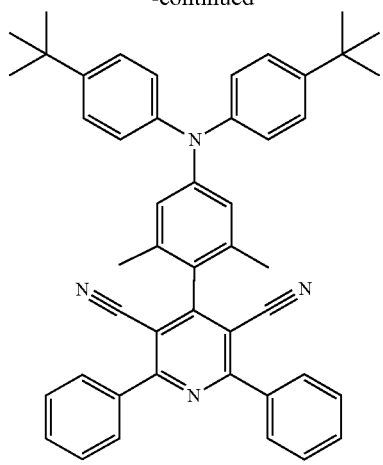
,
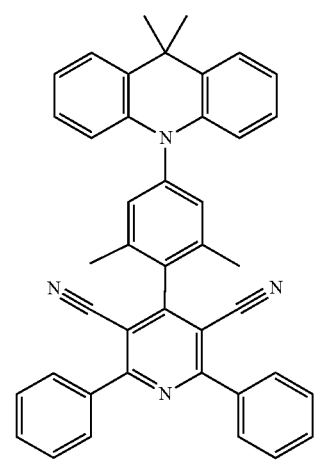
,
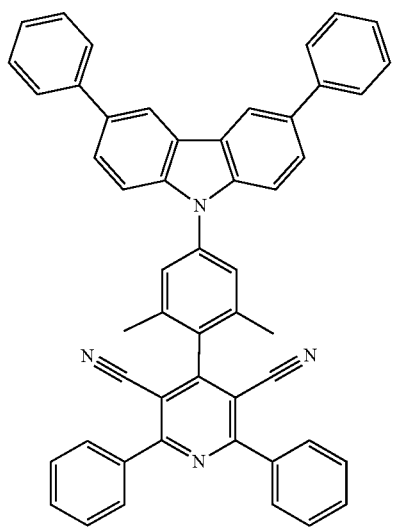 [SMILES: Cc1cc(-n2c3ccc(-c4ccccc4)cc3c3cc(-c4ccccc4)ccc32)cc(C)c1-c1c(C#N)c(-c2ccccc2)nc(-c2ccccc2)c1C#N]
,
16
-continued
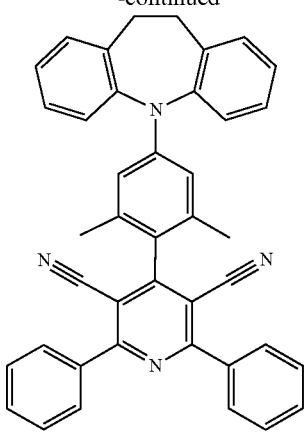
,
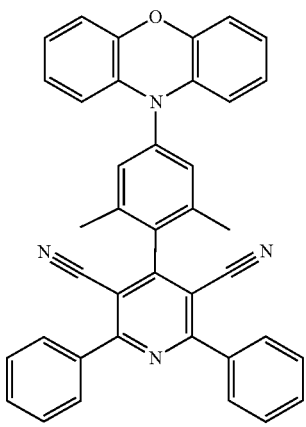
,
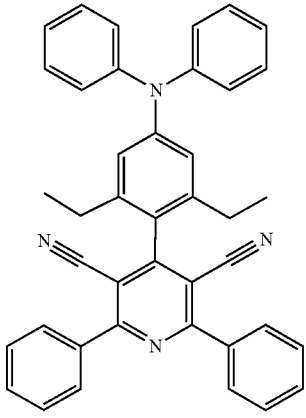 [SMILES: CCc1cc(N(c2ccccc2)c2ccccc2)cc(CC)c1-c1c(C#N)c(-c2ccccc2)nc(-c2ccccc2)c1C#N]
,
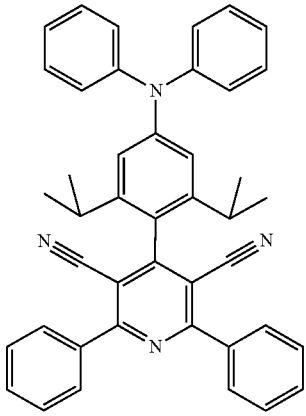 [SMILES: CC(C)c1cc(N(c2ccccc2)c2ccccc2)cc(C(C)C)c1-c1c(C#N)c(-c2ccccc2)nc(-c2ccccc2)c1C#N]
,

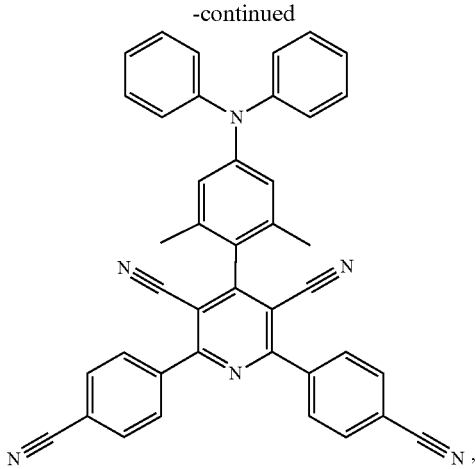

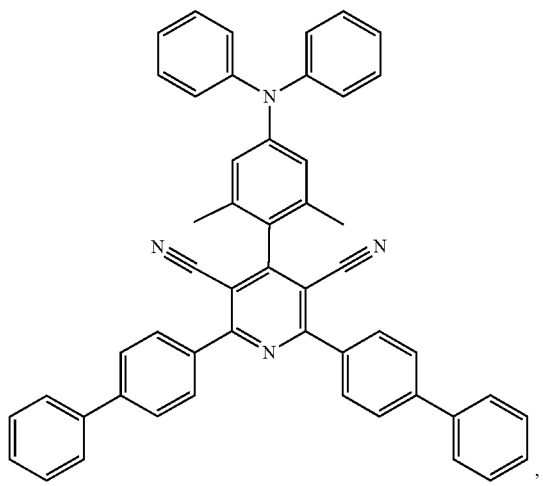

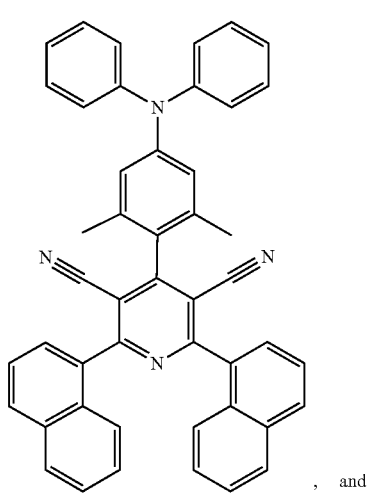
, and

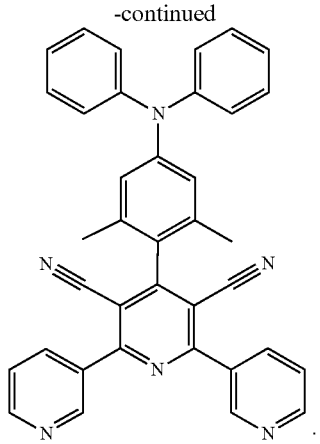

In the present embodiment, the pyridine-carbonitrile compound of the disclosure has pyridine-3,5-dicarbonitrile as a core structure, and this core structure may serve as an electron acceptor (i.e., electron withdrawing group). In addition, in the pyridine-carbonitrile compound of the disclosure, a phenyl group (serving as a linking group) is linked to position 4 of a pyridyl group, and a nitrogen-containing group ($R_3$) serving as an electron donor (i.e., electron donating group) is introduced into the para position of the phenyl group. In addition, in the pyridine-carbonitrile compound of the disclosure, an alkyl group ($R_1$ and $R_2$) is introduced into the ortho position of the phenyl group serving as the linking group, and an aryl group or heteroaryl group having resonance properties is introduced into positions 2 and 6 of the pyridyl group (as the core structure).

Since the pyridyl group itself has insufficient electron withdrawing ability, in the pyridine-carbonitrile compound of the disclosure, by introducing the cyano group into positions 3 and 5 of the pyridyl group, the electron accepting capacity of the pyridyl group is improved. In addition, the pyridine-carbonitrile compound of the disclosure uses pyridine-3,5-dicarbonitrile as an electron withdrawing group to thereby improve the overall charge transfer property of molecules and reduce an electron cloud overlap between the HOMO and the LUMO, so as to reduce $\Delta E_{ST}$. In this way, TADF characteristics are achieved, and luminous efficiency of an OLED element fabricated using the pyridine-carbonitrile compound can be improved.

In addition, in the pyridine-carbonitrile compound of the present embodiment, by introducing the nitrogen-containing group ($R_3$) serving as the electron donor into the para position of the phenyl group serving as the linking group, emission color and photoluminescence quantum yield (PLQY) of the molecules can be controlled. In addition, in the pyridine-carbonitrile compound of the present embodiment, by introducing the alkyl group ($R_1$ and $R_2$) into the ortho position of the phenyl group serving as the linking group, a steric hindrance effect between the alkyl group and the cyano group increases a dihedral angle between the phenyl group and pyridine-3,5-dicarbonitrile, thereby reducing the electron cloud overlap between the HOMO and the LUMO.

An organic light-emitting diode according to one embodiment of the disclosure will be described below with reference to the drawings.

FIG. 1 is a schematic cross-sectional view of an electroluminescent device according to one embodiment of the disclosure.

Referring to FIG. 1, an electroluminescent device 10 of the present embodiment includes an anode 102, a cathode 104, and a light-emitting layer 106. In one embodiment, the electroluminescent device 10 is an organic light-emitting diode (OLED). The light-emitting layer 106 is disposed between the anode 102 and the cathode 104. The anode 102 may be made of a conductor having a high work function, so as to facilitate injection of holes into the light-emitting layer 106. A material of the anode 102 is, for example, a metal, a metal oxide, a conductive polymer, or a combination thereof. Specifically, the metal is, for example, nickel, platinum, vanadium, chromium, copper, zinc, gold or an alloy thereof; the metal oxide is, for example, a zinc oxide, an indium oxide, an indium tin oxide (ITO) or an indium zinc oxide (IZO); a combination of a metal and a metal oxide is, for example, a combination of ZnO and Al or a combination of $SnO_2$ and Sb; the conductive polymer is, for example, poly(3-methylthiophene), poly(3,4-(ethylene-1,2-dioxy)thiophene (PEDT), polypyrrole, or polyaniline. However, the disclosure is not limited thereto.

The cathode 104 may be made of a conductor having a low work function, so as to facilitate injection of electrons into the light-emitting layer 106. A material of the cathode 104 is, for example, a metal or a material having a multilayer structure. Specifically, the metal is, for example, magnesium, calcium, sodium, potassium, titanium, indium, yttrium, lithium, gadolinium, aluminum, silver, tin, lead, cesium, barium or an alloy thereof; the material having a multilayer structure is, for example, LiF/Al, $LiO_2$/Al, LiF/Ca, LiF/Al, or $BaF_2$/Ca. However, the disclosure is not limited thereto.

In the present embodiment, the light-emitting layer 106 includes the pyridine-carbonitrile compound of the aforementioned embodiments. Specifically, the light-emitting layer 106 includes a single kind of the pyridine-carbonitrile compound of the aforementioned embodiments, or at least two kinds of the pyridine-carbonitrile compounds of the aforementioned embodiments, or a mixture of at least one of the pyridine-carbonitrile compounds of the aforementioned embodiments and other compound.

The light-emitting layer 106 generally includes a host light-emitting material and a guest light-emitting material. In one embodiment, the pyridine-carbonitrile compound of the aforementioned embodiments may serve as the host light-emitting material and be mixed with the guest light-emitting material. In one embodiment, the light-emitting layer 106 may include the pyridine-carbonitrile compound and other host light-emitting materials. In one embodiment, the pyridine-carbonitrile compound of the aforementioned embodiments may serve as the guest light-emitting material and be mixed with the host light-emitting material.

The host light-emitting material other than the pyridine-carbonitrile compound of the aforementioned embodiments is, for example, a fused aromatic ring derivative, a heterocycle-containing compound or the like. The fused aromatic ring derivative is, for example, an anthracene compound, a pyrene compound, a naphthalene compound, a pentacene compound, a phenanthrene compound, a fluoranthene compound or the like. The heterocycle-containing compound is, for example, a carbazole compound, a dibenzofuran compound, a ladder-type furan compound, a pyrimidine compound or the like.

The guest light-emitting material other than the pyridine-carbonitrile compound of the aforementioned embodiments is, for example, an arylamine compound, a styrylamine compound, a boron complex, a fluoranthene compound, a metal complex or the like. Specifically, the arylamine compound is, for example, a fused aromatic ring compound substituted with an arylamine group. Examples thereof include pyrene, anthracene, chrysene and periflanthene having an arylamine group. Specific examples of the styrylamine compound include styrylamine, styryldiamine, styryltriamine and styryltetramine. Examples of the metal complex include an iridium complex and a platinum complex. However, the disclosure is not limited thereto.

In one embodiment, the electroluminescent device 10 further includes at least one auxiliary layer. The auxiliary layer is selected from the group consisting of a hole injection layer, a hole transport layer, a hole blocking layer, an exciton blocking layer, an electron injection layer, an electron transport layer, and an electron blocking layer.

Figure 2:
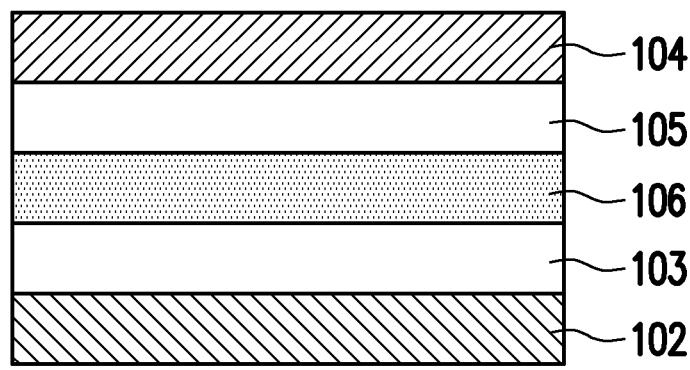
FIG. 2 is a schematic cross-sectional view of an electroluminescent device according to another embodiment of the disclosure.

FIG. 2 is a schematic cross-sectional view of an electroluminescent device according to another embodiment of the disclosure. In FIG. 2, the same elements as those in FIG. 1 will be denoted by the same reference numerals, and the description of the same technical content will be omitted. An electroluminescent device 20 includes the anode 102, a hole transport layer 103, the light-emitting layer 106, an electron transport layer 105, and the cathode 104. In the present embodiment, the light-emitting layer 106 includes the pyridine-carbonitrile compound of the aforementioned embodiments.

The aforementioned embodiments are described in more detail below with reference to examples. However, these examples are not to be construed as limiting the scope of the disclosure in any sense.

Density Functional Theory Calculation

In the present embodiment, through density functional theory (DFT) calculation, geometry optimization is performed on compounds CzmPPC, tCzmPPC, SAcmPPC, TPAmPPC, tTPAmPPC, DPCzmPPC, TPAePPC, TPAiPPC, TPAmPPCcn and TPAmPPCph, and singlet excited state energy ($E_S$), triplet excited state energy ($E_T$), $\Delta E_{ST}$ and dihedral angle of these compounds are obtained, by which the possibility of using the pyridine-carbonitrile compound of the disclosure as a TADF material is predicted.

In the present embodiment, transition energy and electron cloud distribution from a ground state to an excited state are calculated by using Gaussian 09 as calculation software and performing a B3LYP calculation with a 6-31G* basis set according to the time-dependent density functional theory (TD-DFT).

Results of the theoretical calculation are shown in Table 1 below, where the dihedral angle is defined as an angle between pyridine-3,5-dicarbonitrile and the phenyl group in position 4.

TABLE 1

| Compound structure | Es (eV) | $E_T$ (eV) | $\Delta E_{ST}$ (eV) | Dihedral angle (°) |
| --- | --- | --- | --- | --- |
| CzmPPC | 2.716 | 2.648 | 0.068 | 76.9 |
| tCzmPPC | 2.565 | 2.560 | 0.005 | 78.5 |
| SAcmPPC | 2.230 | 2.230 | 0.0001 | 86.1 |

TABLE 1-continued

| Compound structure | Es (eV) | E$_T$ (eV) | ΔE$_{ST}$ (eV) | Dihedral angle (°) |
|---|---|---|---|---|
| TPAmPPC | 2.506 | 2.491 | 0.015 | 73.8 |
| tTPAmPPC | 2.371 | 0.358 | 0.013 | 74.0 |
| DPCzmPPC | 2.583 | 2.580 | 0.003 | 81.7 |

TABLE 1-continued

| Compound structure | Es (eV) | $E_T$ (eV) | $\Delta E_{ST}$ (eV) | Dihedral angle (°) |
|---|---|---|---|---|
| TPAePPC | 2.439 | 2.426 | 0.013 | 82.7 |
| TPAiPPC | 2.439 | 2.428 | 0.011 | 89.3 |
| TPAmPPCcn | 1.991 | 1.976 | 0.015 | 73.7 |

TABLE 1-continued

| Compound structure | Es (eV) | $E_T$ (eV) | $\Delta E_{ST}$ (eV) | Dihedral angle (°) |
|---|---|---|---|---|
| TPAmPPCph | 2.413 | 2.399 | 0.014 | 75.3 |

As can be seen from Table 1, according to the theoretical calculation, a difference $\Delta E_{ST}$ between the singlet excited state energy ($E_S$) and the triplet excited state energy ($E_T$) of the pyridine-carbonitrile compound of the disclosure ranges from 0.0001 eV to 0.078 eV, and the dihedral angle ranges from 73.7° to 89.1°. The reason behind the low $\Delta E_{ST}$ and large dihedral angle as above is that, in the pyridine-carbonitrile compound, steric hindrance between the alkyl group in the ortho position of the phenyl group and the cyano group in positions 3 and 5 of the pyridyl group staggers two planes so that they are nearly orthogonal to each other, the overlap between the HOMO and LUMO orbitals is reduced, thereby reducing $\Delta E_{ST}$. Therefore, it can be inferred that the pyridine-carbonitrile compound of the disclosure has TADF characteristics.

In the present embodiment, the compounds TPAPPC and TPAsPPC are used as comparative examples. In the structure of the compound TPAPPC, no substituent is present in the ortho position ($R_1$ and $R_2$) of the phenyl ring linked to the pyridine-3,5-dicarbonitrile. That is, $R_1$ and $R_2$ are both hydrogen. In the structure of the compound TPAsPPC, $R_1$ is hydrogen and $R_2$ is a methyl group.

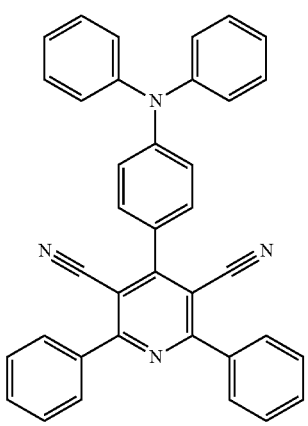

TPAPPC

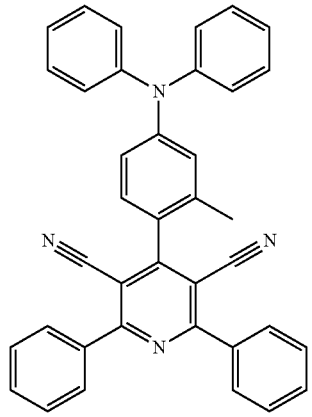

-continued

TPAsPPC

Through DFT calculation, electron cloud distributions, $\Delta E_{ST}$ and dihedral angles of molecular orbitals (MOs) of the compounds TPAPPC, TPAsPPC and TPAmPPC are obtained. Results of the theoretical calculation are shown in Table 2 below.

TABLE 2

| Compound | $\Delta E_{ST}$ (eV) | Dihedral angle (°) |
|---|---|---|
| TPAPPC | 0.224 | 50.4 |
| TPAsPPC | 0.025 | 68.2 |
| TPAmPPC | 0.015 | 73.8 |

Figure 3:
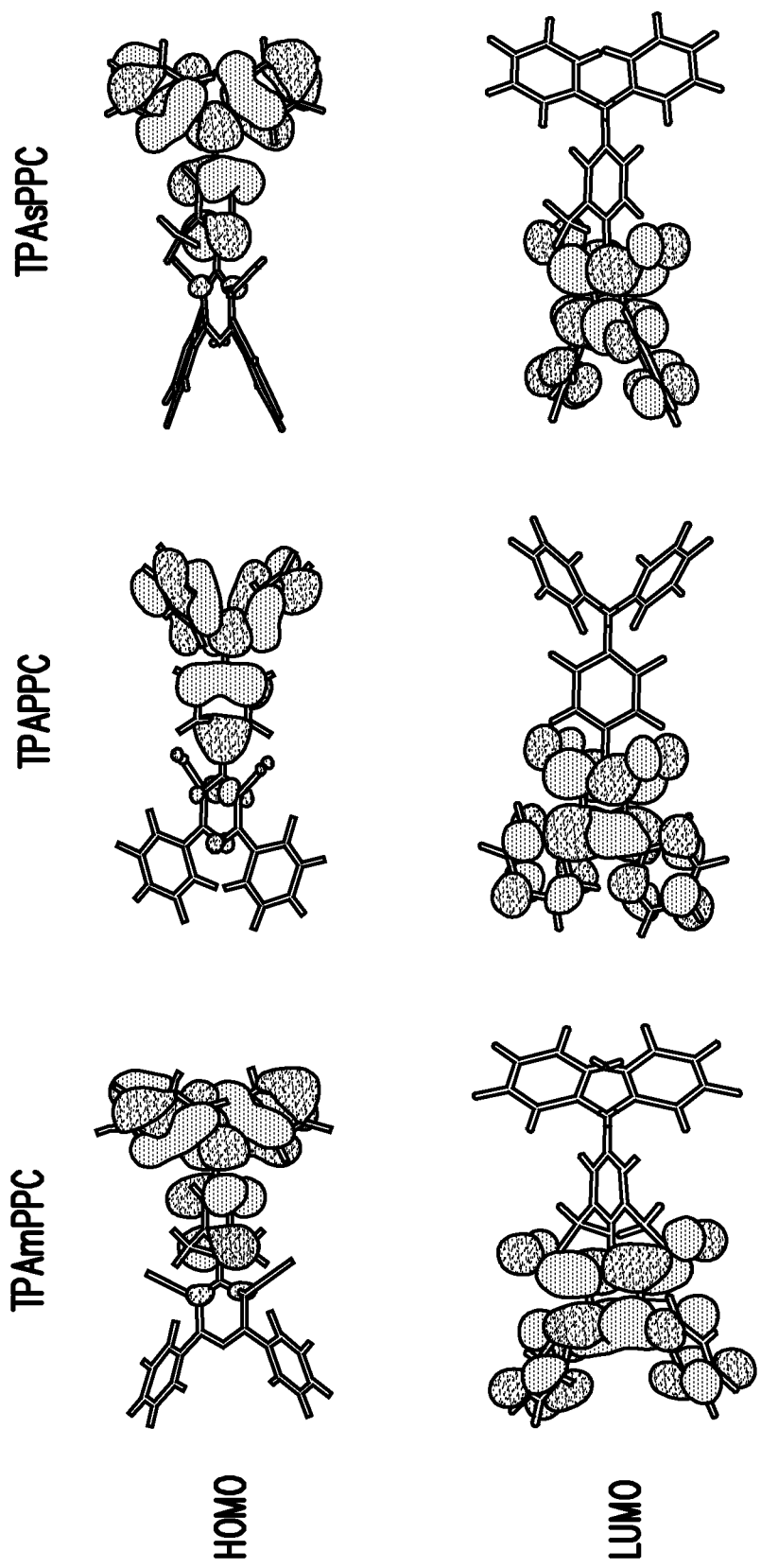
FIG. 3 shows electron cloud distributions of molecular orbitals (MOs) of TPAPPC, TPAsPPC and TPAmPPC.

FIG. 3 shows the electron cloud distributions of the MOs of TPAPPC, TPAsPPC and TPAmPPC. As can be seen from Table 2 and FIG. 3, in the compound TPAmPPC, the electron clouds of the HOMO are mainly distributed on an electron acceptor (i.e., electron withdrawing group), and the electron clouds of the LUMO are mainly distributed on an electron donor (i.e., electron donating group). In addition, in the compound TPAmPPC, since the alkyl group in the ortho position of the phenyl group is close to the pyridyl group, the alkyl group on the phenyl group creates steric hindrance with the cyano group on the pyridyl group, such that the HOMO and the LUMO are well separated (i.e., the overlap between the HOMO and LUMO orbitals is small), and $\Delta E_{ST}$ is thus reduced (to only 0.015).

In contrast, in the compounds TPAPPC and TPAsPPC, due to the lack of sufficient steric hindrance at the ortho position of the linking group (i.e., phenyl group), the dihedral angle is only 50.4° to 68.2°. Moreover, the electron clouds of the HOMO may extend onto the pyridyl group, thus increasing the overlap between the HOMO and LUMO orbitals and increasing $\Delta E_{ST}$.

Synthesis of Organic Compound
Synthesis of Intermediate Product

Synthesis Example 1

Synthesis of Intermediate Product I-1 (4-(9H-carbazol-9-yl)-2,6-dimethylbenzaldehyde)

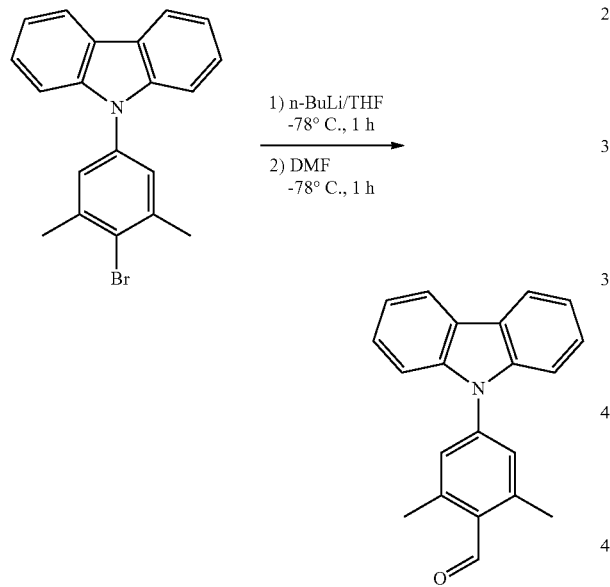

Reaction Scheme 1

A compound 9-(4-bromo-3,5-dimethylphenyl)-9H-carbazole (1 g, 2.9 mmol) was placed in a double-necked flask, sealed with a serum stopper, dry tetrahydrofuran (THF) (19 mL, 0.15 M) was added from a side port, and the system was cooled to −78° C. in an acetone bath. Under nitrogen, n-butyllithium (n-BuLi) (1.73 mL, 4.3 mmol) was slowly added with a plastic syringe to obtain an orange solution, and the solution was kept in the acetone bath for 1 hour. Next, under nitrogen, dry dimethylformamide (DMF) (0.64 g, 8.7 mmol) was added with a syringe, and the solution was kept in the acetone bath for another 1 hour, and then reacted overnight. After the reaction was over, water was added, and excess alkali was neutralized with a hydrochloric acid aqueous solution. Ethyl acetate extraction was performed three times, followed by rotary concentration. Then, the mixture was purified by column chromatography (eluent: ethyl acetate/n-hexane=1/19, v/v), and Intermediate Product I-1 (0.69 g, yield: 80.0%) in the form of a white solid was obtained.

$^1$H NMR (500 MHz, CDCl$_3$, δ): 10.67 (s, 1H), 8.12 (d, J=8.0 Hz, 2H), 7.48 (d, J=8.5 Hz, 2H), 7.42 (t, J=8.0 Hz, 2H), 7.34 (s, 2H), 7.30 (t, J =7.5 Hz, 2H), 2.72 (s, 6H). $^{13}$C NMR (125 MHz, CDCl$_3$, δ): 192.41, 143.51, 141.58, 140.11, 130.91, 127.17, 126.13, 123.79, 120.52, 120.43, 109.92, 20.80.

Synthesis Example 2

Synthesis of Intermediate Product I-2 (4-(3, 6-di-tert-butyl-9H-carbazol-9-yl)-2, 6-dimethylbenzaldehyde)

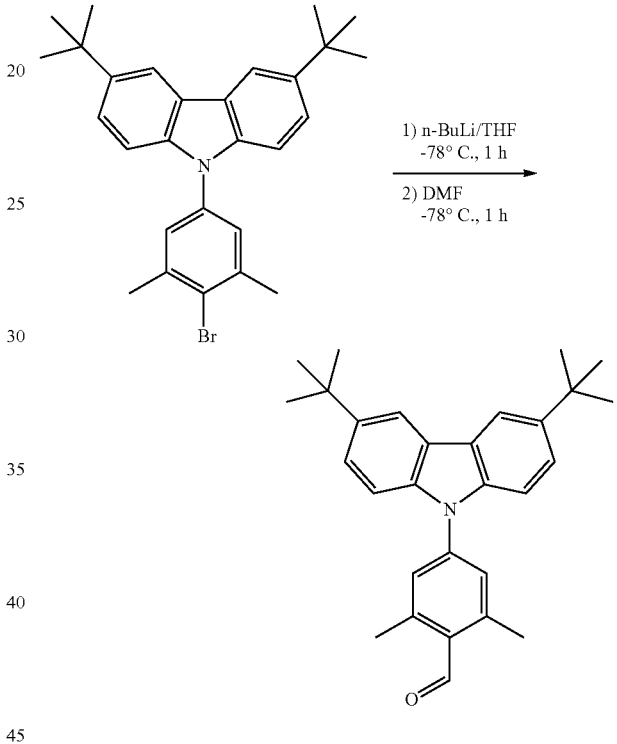

Reaction Scheme 2

A compound 9-(4-bromo-3,5-dimethylphenyl)-3,6-di-tert-butyl-9H-carbazole (1 g, 2.2 mmol) was placed in a double-necked flask, sealed with a serum stopper, dry THF (14 mL, 0.15 M) was added from a side port, and the system was cooled to −78° C. in an acetone bath. Under nitrogen, n-BuLi (1.31 mL, 3.2 mmol) was slowly added with a plastic syringe to obtain an orange solution, and the solution was kept in the acetone bath for 1 hour. Next, under nitrogen, dry DMF (0.47 g, 6.5 mmol) was added with a syringe, and the solution was kept in the acetone bath for another 1 hour, and then reacted overnight. After the reaction was over, water was added, and excess alkali was neutralized with a hydrochloric acid aqueous solution. Ethyl acetate extraction was performed three times, followed by rotary concentration. Then, the mixture was purified by column chromatography (eluent: ethyl acetate/n-hexane=1/19, v/v), and Intermediate Product I-2 (0.6 g, yield: 67.4%) in the form of a white solid was obtained.

$^1$H NMR (500 MHz, CDCl$_3$, δ): 10.66 (s, 1H), 8.12 (s, 2H), 7.45 (q, J=8.5 Hz, 4H), 7.33 (s, 2H), 2.71 (s, 6H), 1.45 (s, 18H). $^{13}$C NMR (125 MHz, CDCl$_3$, δ): 192.34, 143.56, 143.47, 142.13, 138.38, 130.39, 126.58, 123.87, 123.78, 116.37, 109.44, 34.75, 31.95, 20.84.

Synthesis Example 3

Synthesis of Intermediate Product I-3 (4-(5H-dibenzo[b,f]azepin-5-yl)-2,6-dimethylbenzaldehyde)

Reaction Scheme 3

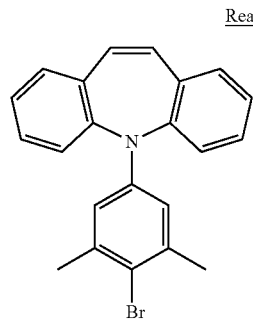

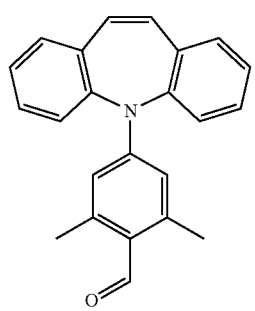

A compound 5-(4-bromo-3,5-dimethylphenyl)-5H-dibenzo[b,f]azepine (0.3 g, 0.8 mmol) was placed in a double-necked flask, sealed with a serum stopper, dry THF (8 mL, 0.1 M) was added from a side port, and the system was cooled to −78° C. in an acetone bath. Under nitrogen, n-BuLi (0.48 mL, 1.8 mmol) was slowly added with a plastic syringe to obtain an orange solution, and the solution was kept in the acetone bath for 1 hour. Next, under nitrogen, dry DMF (0.18 g, 2.4 mmol) was added with a syringe, and the solution was kept in the acetone bath for another 1 hour, and then reacted overnight. After the reaction was over, water was added, and excess alkali was neutralized with a hydrochloric acid aqueous solution. Ethyl acetate extraction was performed three times, followed by rotary concentration. Then, the mixture was purified by column chromatography (eluent: ethyl acetate/n-hexane=1/19, v/v), and Intermediate Product I-3 (0.14 g, yield: 53.3%) in the form of a yellow solid was obtained.

$^1$H NMR (500 MHz, CDCl$_3$, δ): 10.28 (s, 1H), 7.51 (t, J=7.5 Hz, 2H), 7.44 (d, J=8.0 Hz, 4H), 7.38 (t, J=7.5 Hz, 2H), 6.85 (s, 2H), 5.91 (s, 2H), 2.37 (s, 6H). $^{13}$C NMR (125 MHz, CDCl$_3$, δ): 190.76, 151.93, 143.82, 141.45, 135.72, 130.45, 130.32, 129.83, 129.48, 127.57, 123.53, 112.27, 21.42.

Synthesis Example 4

Synthesis of Intermediate Product I-4

(2,6-dimethyl-4-(10H-spiro [acridine-9,9'-fluoren]-10-yl)benzaldehyde)

Reaction Scheme 4

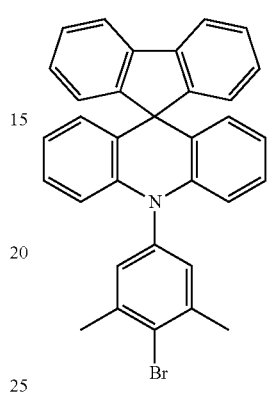

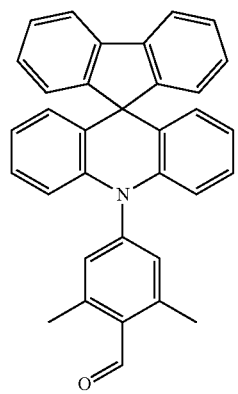

A compound 10-(4-bromo-3,5-dimethylphenyl)-10H-spiro [acridine-9,9'-fluorene] (1 g, 1.9 mmol) was placed in a double-necked flask, sealed with a serum stopper, dry THF (24 mL, 0.08 M) was added from a side port, and the system was cooled to −78° C. in an acetone bath. Under nitrogen, n-BuLi (1.16 mL, 2.9 mmol) was slowly added with a plastic syringe to obtain an orange solution, and the solution was kept in the acetone bath for 1 hour. Next, under nitrogen, dry DMF (0.43 g, 5.7 mmol) was added with a syringe, and the solution was kept in the acetone bath for another 1 hour, and then reacted overnight. After the reaction was over, water was added, and excess alkali was neutralized with a hydrochloric acid aqueous solution. Ethyl acetate extraction was performed three times, followed by rotary concentration. Then, the mixture was purified by column chromatography (eluent: ethyl acetate/n-hexane=1/19, v/v), and Intermediate Product I-4 (0.61 g, yield: 67.2%) in the form of a yellow solid was obtained.

$^1$H NMR (500 MHz, CDCl$_3$, δ): 10.72 (s, 1H), 7.77 (d, J=7.5 Hz, 2H), 7.38-7.33 (m, 4H), 7.23-7.21 (m, 4H), 6.90 (t, J=7.5 Hz, 2H), 6.55 (t, J=7.5 Hz, 2H), 6.38 (d, J=7.5 Hz, 2H), 6.34 (d, J=7.5 Hz, 2H), 2.72 (s, 6H). $^{13}$C NMR (125 MHz, CDCl$_3$, δ): 192.87, 156.52, 144.96, 144.44, 140.59, 139.19, 132.40, 132.13, 128.37, 127.96, 127.62, 127.23, 125.72, 124.80, 120.86, 119.91, 114.46, 20.67.

Synthesis Example 5

Synthesis of Intermediate Product I-5 (4-(diphenylamino)-2,6-dimethylbenzaldehyde)

Reaction Scheme 5

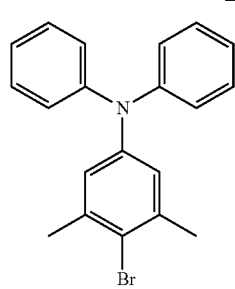

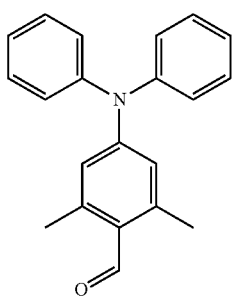

A compound 4-bromo-3,5-dimethyl-N,N-diphenylaniline (1 g, 2.8 mmol) was placed in a double-necked flask, sealed with a serum stopper, dry THF (28 mL, 0.1 M) was added from a side port, and the system was cooled to −78° C. in an acetone bath. Under nitrogen, n-BuLi (1.7 mL, 4.3 mmol) was slowly added with a plastic syringe to obtain an orange solution, and the solution was kept in the acetone bath for 1 hour. Next, under nitrogen, dry DMF (0.64 g, 8.7 mmol) was added with a syringe, and the solution was kept in the acetone bath for another 1 hour, and then reacted overnight. After the reaction was over, water was added, and excess alkali was neutralized with a hydrochloric acid aqueous solution. Ethyl acetate extraction was performed three times, followed by rotary concentration. Then, the mixture was purified by column chromatography (eluent: ethyl acetate/n-hexane=1/19, v/v), and Intermediate Product I-5 (0.66 g, yield: 77.4%) in the form of a pale yellow solid was obtained.

$^1$H NMR (500 MHz, CDCl$_3$, δ): 10.39 (s, 1H), 7.31 (t, J=8.0 Hz, 4H), 7.15-7.12 (m, 6H), 6.58 (s, 2H), 2.47 (s, 6H). $^{13}$C NMR (125 MHz, CDCl$_3$, δ): 191.18, 151.60, 146.22, 143.61, 129.58, 126.26, 125.39, 124.76, 120.27, 21.10.

Synthesis Example 6

Synthesis of Intermediate Product I-6 (4-(bis(4-(tert-butyl)phenyl)amino)-2,6-dimethylbenzaldehyde)

Reaction Scheme 6

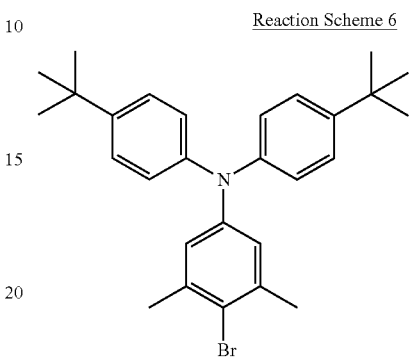

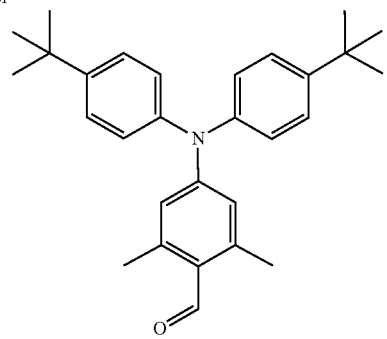

A compound 4-bromo-N,N-bis(4-(tert-butyl)phenyl)-3,5-dimethylaniline (0.5 g, 1.1 mmol) was placed in a double-necked flask, sealed with a serum stopper, dry THF (11 mL, 0.1 M) was added from a side port, and the system was cooled to −78° C. in an acetone bath. Under nitrogen, n-BuLi (0.6 mL, 1.6 mmol) was slowly added with a plastic syringe to obtain an orange solution, and the solution was kept in the acetone bath for 1 hour. Next, under nitrogen, dry DMF (0.2 g, 3.2 mmol) was added with a syringe, and the solution was kept in the acetone bath for another 1 hour, and then reacted overnight. After the reaction was over, water was added, and excess alkali was neutralized with a hydrochloric acid aqueous solution. Ethyl acetate extraction was performed three times, followed by rotary concentration. Then, the mixture was purified by column chromatography (eluent: ethyl acetate/n-hexane=1/19, v/v), and Intermediate Product I-6 (0.4 g, yield: 88.0%) in the form of a yellow solid was obtained.

$^1$H NMR (500 MHz, CDCl$_3$, δ): 10.38 (s, 1H), 7.31 (d, J=8.4 Hz, 4H), 7.05 (d, J=8.4 Hz, 4H), 6.55 (s, 2H), 2.48 (s, 6H), 1.32 (s, 18H). $^{13}$C NMR (125 MHz, CDCl$_3$, δ): 190.98, 151.90, 147.79, 143.61, 143.28, 126.40, 125.89, 124.64, 119.15, 34.44, 31.37, 21.19.

Synthesis Example 7

Synthesis of Intermediate Product I-7 (4-(diphenylamino)-benzaldehyde)

Synthesis of Final Compound

Synthesis Example 8

Synthesis of Compound 4-(4-(9H-carbazol-9-yl)-2,6-dimethylphenyl)-2,6-diphenylpyridine-3,5-dicarbonitrile (CzmPPC)

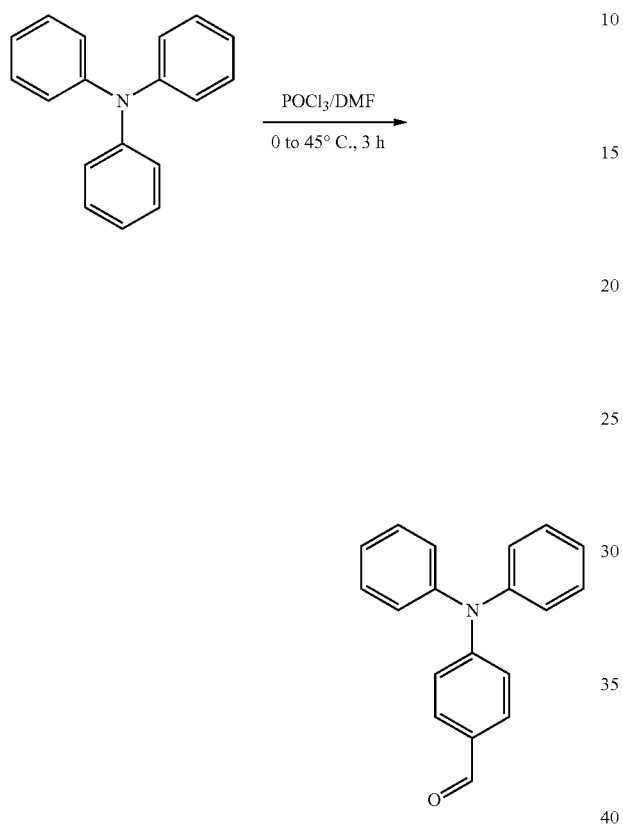

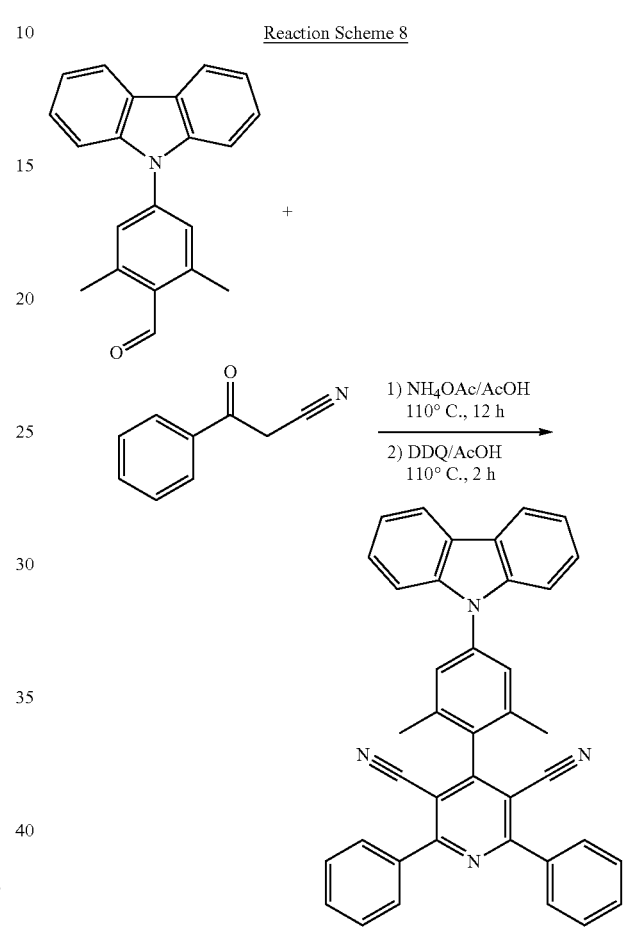

Triphenylamine (2 g, 8.2 mmol) was placed in a double-necked flask, dry DMF (12 mL, 0.4 M) was added with a syringe, vacuuming and filling were performed three times, and the system was cooled to 0° C. Under nitrogen, phosphoryl trichloride (POCl₃) (6.3 g, 40.8 mmol) was slowly added with a plastic syringe, and the ice bath was removed. After room temperature was reached, the mixture was heated at 45° C. for 3 hours. After the reaction was over, a large amount of ice water was added to terminate the reaction, and a yellow solid precipitate was collected in a ceramic funnel. Then, the mixture was purified by column chromatography (eluent: ethyl acetate/n-hexane=1/19, v/v), and Intermediate Product I-7 (1.98 g, yield: 88.8%) in the form of a yellow solid was obtained.

$^1$H NMR (500 MHz, CDCl₃, δ): 10.39 (s, 1H), 7.31 (t, J=8.0 Hz, 4H), 7.15-7.12 (m, 6H), 6.58 (s, 2H), 2.47 (s, 6H). $^{13}$C NMR (125 MHz, CDCl₃, δ): 191.18, 151.60, 146.22, 143.61, 129.58, 126.26, 125.39, 124.76, 120.27, 21.10.

Intermediate Product I-7 (0.67 g, 2.2 mmol), benzoylacetonitrile (0.81 g, 5.6 mmol), and ammonium acetate (0.43 g, 5.6 mmol) were placed in a double-necked flask, acetic acid (6.7 mL) was added as a solvent, and the mixture was heated to 110° C. and refluxed for 12 hours. After the reaction was over and the mixture was returned to room temperature, 2,3-dichloro-5,6-dicyano-p-benzoquinone (1.5 g, 6.6 mmol) was added in the double-necked flask, heated to 110° C., and refluxed for 2 hours for oxidation reaction. After the reaction was over and the mixture was returned to room temperature, suction filtration was performed, excess acetic acid was removed by washing with water, the solvent and water were removed by high vacuum, and a crude product was obtained. The crude product was purified by column chromatography and CzmPPC (0.69 g, total yield: 57.2%) in the form of a white solid was obtained as a product. Finally, the product was refined in a sublimation machine under high vacuum (5×10⁻⁶ torr) at a sublimation temperature of 240° C.

$^1$H NMR (500 MHz, CDCl₃, δ): 8.19-8.15 (m, 6H), 7.62-7.61 (m, 6H), 7.55 (d, J=8.0 Hz, 2H), 7.51 (s, 2H), 7.46 (t, J=8.0 Hz, 2H), 7.31 (t, J =7.5 Hz, 2H), 2.31 (s, 6H). $^{13}$C NMR (125 MHz, CDCl₃, δ): 163.12, 160.71, 140.56, 139.36, 137.12, 136.06, 132.50, 131.68, 129.52, 128.91, 126.75, 126.04, 123.50, 120.28, 120.15, 115.05, 110.01, 106.45, 20.29. HRMS (FD) m/z: [M+] calcd. for $C_{39}H_{26}N_4$, 550.2152; found, 550.2151. Anal. calcd. for $C_{39}H_{26}N_4$: C 85.07, H 4.76, N 10.17 found: C 85.17, H 4.51, N 10.03.

Synthesis Example 9

Synthesis of Compound 4-(4-(3,6-di-tert-butyl-9H-carbazol-9-yl)-2,6-dimethylphenyl)-2,6-diphenylpyridine-3,5-dicarbonitrile (tCzmPPC)

Reaction Scheme 9

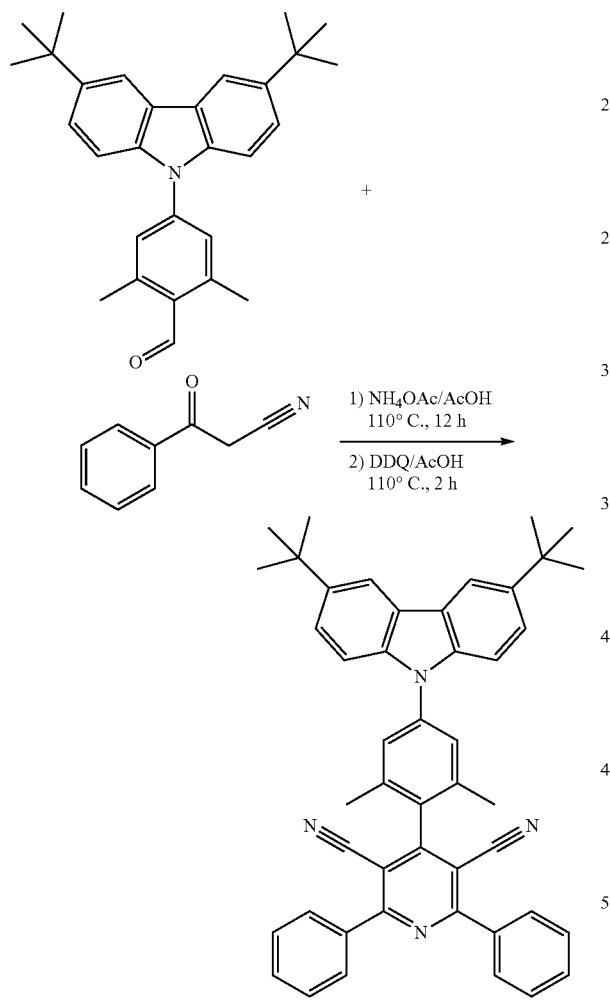

Intermediate Product I-2 (0.2 g, 0.5 mmol), benzoylacetonitrile (0.18 g, 1.2 mmol), and ammonium acetate (0.11 g, 1.5 mmol) were placed in a double-necked flask, acetic acid (5 mL) was added as a solvent, and the mixture was heated to 110° C. and refluxed for 12 hours. After the reaction was over and the mixture was returned to room temperature, 2,3-dichloro-5,6-dicyano-p-benzoquinone (0.34 g, 1.5 mmol) was added in the double-necked flask, heated to 110° C., and refluxed for 2 hours for oxidation reaction. After the reaction was over and the mixture was returned to room temperature, suction filtration was performed, excess acetic acid was removed by washing with water, the solvent and water were removed by high vacuum, and a crude product was obtained. The crude product was purified by column chromatography and tCzmPPC (0.23 g, total yield: 68.1%) was obtained as a product. Finally, the product was refined in a sublimation machine under high vacuum ($5 \times 10^{-6}$ torr) at a sublimation temperature of 265° C.

$^1$H NMR (500 MHz, CDCl$_3$, δ): 8.15-8.13 (m, 6H), 7.60 (m, 6H), 7.48 (m, 6H), 2.27 (s, 6H), 1.46 (s, 18H). $^{13}$C NMR (125 MHz, CDCl$_3$, δ): 163.10, 160.84, 143.10, 139.89, 138.89, 136.92, 136.11, 131.90, 131.65, 129.53, 128.91, 126.24, 123.69, 123.54, 116.20, 115.06, 109.49, 106.57, 34.73, 31.99, 20.29. HRMS (FD) m/z: [M+] calcd. for $C_{47}H_{42}N_4$, 662.3404; found, 662.3405. Anal. calcd. for $C_{47}H_{42}N_4$: C 85.16, H 6.39, N 8.45 found: C 85.56, H 5.98, N 8.51.

Synthesis Example 10

Synthesis of Compound 4-(4-(5H-dibenzo [b,f] azepin-5-yl)-2, 6-dimethylphenyl)-2,6-diphenylpyridine-3,5-dicarbonitrile (DBAZmPPC)

Reaction Scheme 10

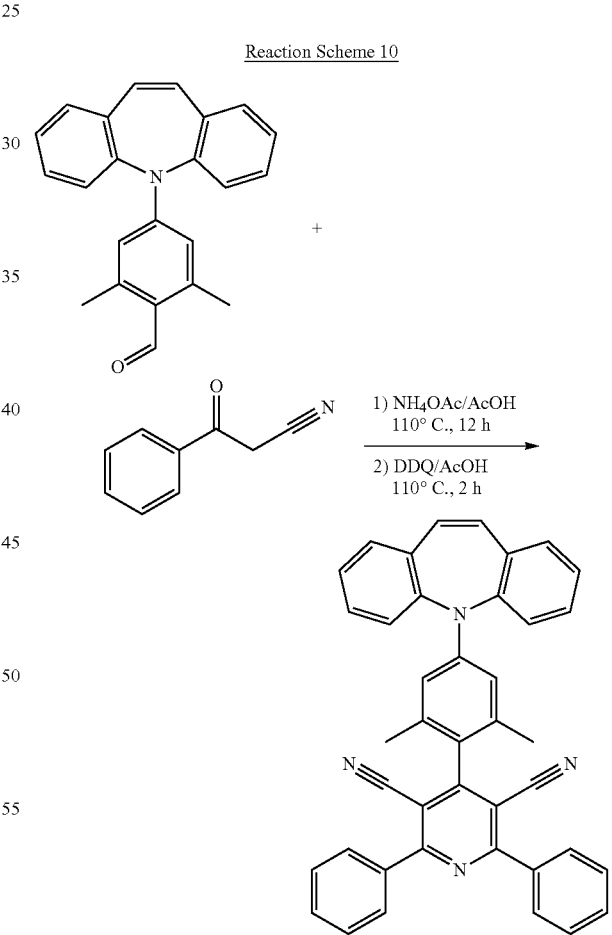

Intermediate Product I-3 (0.2 g, 0.6 mmol), benzoylacetonitrile (0.22 g, 1.5 mmol), and ammonium acetate (0.14 g, 1.8 mmol) were placed in a double-necked flask, acetic acid (5.5 mL) was added as a solvent, and the mixture was heated to 110° C. and refluxed for 12 hours. After the reaction was over and the mixture was returned to room temperature, 2,3-dichloro-5,6-dicyano-p-benzoquinone (0.41 g, 1.8 mmol) was added in the double-necked flask, heated to 110° C., and oxidation reaction was performed for 2 hours. After the reaction was over and the mixture was returned to room temperature, suction filtration was performed, excess acetic acid was removed by washing with water, the solvent and water were removed by high vacuum, and a crude product was obtained. The crude product was purified by column chromatography and DBAZmPPC (0.21 g, total yield: 60.3%) having a yellow color was obtained as a product. Finally, the product was refined in a sublimation machine under high vacuum ($5\times10^{-6}$ torr) at a sublimation temperature of 260° C.

$^1$H NMR (500 MHz, CDCl$_3$, δ): 8.05 (d, J=7.5 Hz, 4H), 7.54-7.52 (m, 8H), 7.49 (t, J=8.0 Hz, 2H), 7.44 (d, J=7.5 Hz, 2H), 7.35 (t, J=7.5 Hz, 2H), 6.87 (s, 2H), 6.11 (s, 2H), 1.92 (s, 6H). $^{13}$C NMR (125 MHz, CDCl$_3$, δ): 162.75, 162.23, 149.75, 142.44, 136.36, 136.30, 135.13, 131.27, 130.67, 130.21, 130.20, 129.60, 129.45, 128.74, 127.11, 123.09, 115.44, 111.51, 107.58, 20.48. HRMS (FD) m/z: [M$^+$] calcd. for C$_{41}$H$_{28}$N$_4$, 576.2309; found, 576.2303. Anal. calcd. for C$_{41}$H$_{28}$N$_4$: C 85.39, H 4.89, N 9.72 found: C 85.23, H 4.66, N 9.70.

Synthesis Example 11

Synthesis of Compound 2,6-dimethyl-4-(10H-spiro[acridine-9,9'-fluoren]-10-yl)phenyl)-2,6-diphenylpyridine-3,5-dicarbonitrile (SAcmPPC)

Reaction Scheme 11

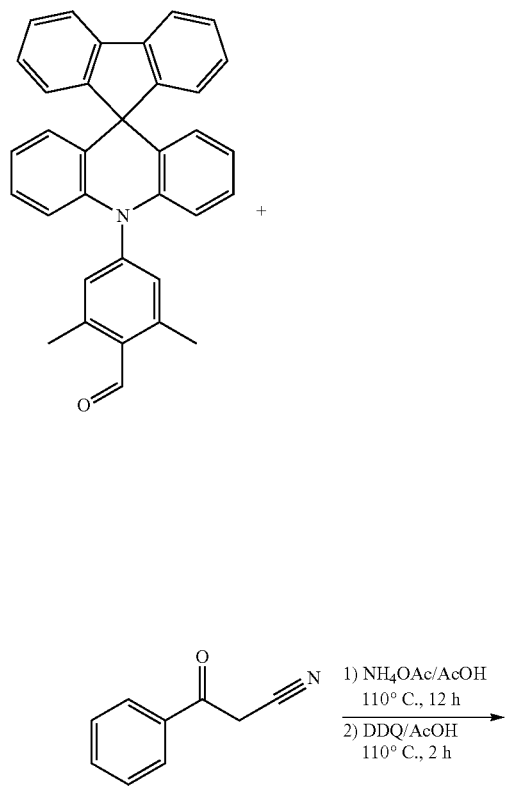

Intermediate Product I-4 (0.2 g, 0.4 mmol), benzoylacetonitrile (0.16 g, 1.1 mmol), and ammonium acetate (0.1 g, 1.3 mmol) were placed in a double-necked flask, acetic acid (5.5 mL) was added as a solvent, and the mixture was heated to 110° C. and refluxed for 12 hours. After the reaction was over and the mixture was returned to room temperature, 2,3-dichloro-5,6-dicyano-p-benzoquinone (0.27 g, 1.2 mmol) was added in the double-necked flask, heated to 110° C., and refluxed for 2 hours for oxidation reaction. After the reaction was over and the mixture was returned to room temperature, suction filtration was performed, excess acetic acid was removed by washing with water, the solvent and water were removed by high vacuum, and a crude product was obtained. The crude product was purified by column chromatography and SAcmPPC (0.15 g, total yield: 51.4%) having a yellow color was obtained as a product. Finally, the product was refined in a sublimation machine under high vacuum ($5\times10^{-6}$ torr) at a sublimation temperature of 310° C.

$^1$H NMR (500 MHz, CDCl$_3$, δ): 8.19 (d, J=7.5 Hz, 4H), 7.79 (d, J=7.5 Hz, 2H), 7.62-7.61 (m, 6H), 7.43-7.42 (m, 4H), 7.37 (t, J=7.5 Hz, 2H), 7.26 (d, J=7.5 Hz, 2H), 6.98 (t, J=7.5 Hz, 2H), 6.58 (t, J=7.5 Hz, 2H), 6.49 (d, J=8.5 Hz, 2H), 6.41 (d, J=8.0 Hz, 2H), 2.33 (s, 6H). $^{13}$C NMR (125 MHz, CDCl$_3$, δ): 163.09, 160.88, 156.52, 142.69, 140.93, 139.21, 138.48, 136.07, 133.97, 131.74, 131.10, 129.55, 129.53, 128.95, 128.35, 127.73, 127.57, 127.48, 125.77, 124.75, 120.76, 119.88, 115.06, 114.67, 106.37, 20.27. HRMS (FD) m/z: [M$^+$] calcd. for C$_{52}$H$_{34}$N$_4$, 714.2778; found, 714.2783. Anal. calcd. for C$_{52}$H$_{34}$N$_4$: C 87.37, H 4.79, N 7.84 found: C 87.56, H 4.38, N 7.91.

Synthesis Example 12

Synthesis of Compound 4-(4-(diphenylamino)-2,6-dimethylphenyl)-2,6-diphenylpyridine-3,5-dicarbonitrile (TPAmPPC)

Reaction Scheme 12

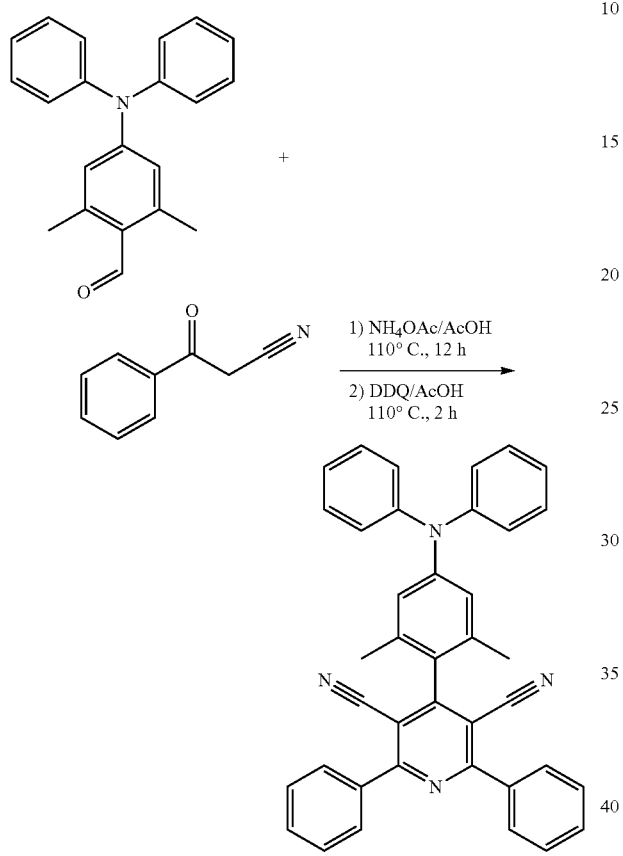

Intermediate Product I-5 (0.2 g, 0.7 mmol), benzoylacetonitrile (0.24 g, 1.7 mmol), and ammonium acetate (0.15 g, 2.0 mmol) were placed in a double-necked flask, acetic acid (6 mL) was added as a solvent, and the mixture was heated to 110° C. and refluxed for 12 hours. After the reaction was over and the mixture was returned to room temperature, 2,3-dichloro-5,6-dicyano-p-benzoquinone (0.48 g, 2.1 mmol) was added in the double-necked flask, heated to 110° C., and refluxed for 2 hours for oxidation reaction. After the reaction was over and the mixture was returned to room temperature, suction filtration was performed, excess acetic acid was removed by washing with water, the solvent and water were removed by high vacuum, and a crude product was obtained. The crude product was purified by column chromatography and TPAmPPC (0.21 g, total yield: 54.1%) was obtained as a product. Finally, the product was refined in a sublimation machine under high vacuum ($5 \times 10^{-6}$ torr) at a sublimation temperature of 230° C.

$^1$H NMR (500 MHz, CDCl$_3$, δ): 8.10 (d, J=7.5 Hz, 4H), 7.57-7.56 (m, 6H), 7.29 (t, J=7.5 Hz, 4H), 7.16 (d, J=8.0 Hz, 4H), 7.06 (t, J=7.5 Hz, 2H), 6.87 (s, 2H), 2.04 (s, 6H). $^{13}$C NMR (125 MHz, CDCl$_3$, δ): 162.85, 161.70, 149.20, 147.18, 136.21, 135.84, 131.41, 129.45, 129.38, 128.78, 126.68, 125.36, 123.54, 121.41, 115.27, 107.11, 20.21. HRMS (FD) m/z: [M$^+$] calcd. for C$_{39}$H$_{28}$N$_4$, 552.2309; found, 552.2313. Anal. calcd. for C$_{39}$H$_{28}$N$_4$: C 84.76, H 5.11, N 10.14 found: C 85.09, H 4.78, N 10.08.

Synthesis Example 13

Synthesis of Compound 4-(4-(Bis(4-(tert-butyl)phenyl)amino)-2,6-dimethylphenyl)-2,6-diphenylpyridine-3,5-dicarbonitrile (tTPAmPPC)

Reaction Scheme 13

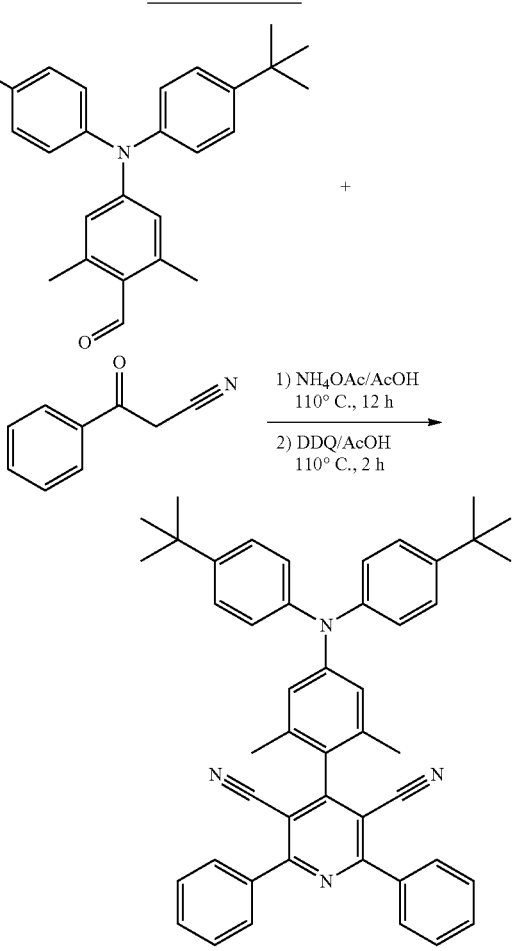

Intermediate Product I-6 (0.4 g, 0.9 mmol), benzoylacetonitrile (0.4 g, 2.4 mmol), and ammonium acetate (0.2 g, 2.9 mmol) were placed in a double-necked flask, acetic acid (15 mL) was added as a solvent, and the mixture was heated to 110° C. and refluxed for 12 hours. After the reaction was over and the mixture was returned to room temperature, 2,3-dichloro-5,6-dicyano-p-benzoquinone (0.61 g, 2.7 mmol) was added in the double-necked flask, heated to 110° C., and refluxed for 2 hours for oxidation reaction. After the reaction was over and the mixture was returned to room temperature, suction filtration was performed, excess acetic acid was removed by washing with water, the solvent and water were removed by high vacuum, and a crude product was obtained. The crude product was purified by column chromatography and tTPAmPPC (0.34 g, total yield: 57.0%) was obtained as a product. Finally, the product was refined in a sublimation machine under high vacuum ($5\times10^{-6}$ torr) at a sublimation temperature of 260° C.

$^1$H NMR (500 MHz, CDCl$_3$, δ): 8.10 (d, J=7.2 Hz, 4H), 7.57-7.56 (m, 6H), 7.29 (d, J=7.8 Hz, 4H), 7.09 (d, J=7.9 Hz, 4H), 6.85 (s, 2H), 2.05 (s, 6H), 1.32 (s, 18H). $^{13}$C NMR (125 MHz, CDCl$_3$, δ): 162.83, 161.95, 149.55, 146.31, 144.47, 136.30, 135.64, 131.37, 129.49, 128.80, 126.17, 125.97, 124.90, 120.78, 115.34, 34.33, 31.42, 20.27. HRMS (EI) m/z: [M+] calcd. for $C_{47}H_{44}N_4$, 664.3566; found, 664.3564. Anal. calcd. for $C_{47}H_{44}N_4$: C 84.90, H 6.67, N 8.43 found: C 84.78, H 6.55, N 8.33.

Synthesis Comparative Example 1

Synthesis of Compound 4-(4-(diphenylamino)phenyl)-2,6-diphenylpyridine-3,5-dicarbonitrile (TPAPPC)

Reaction Scheme 14

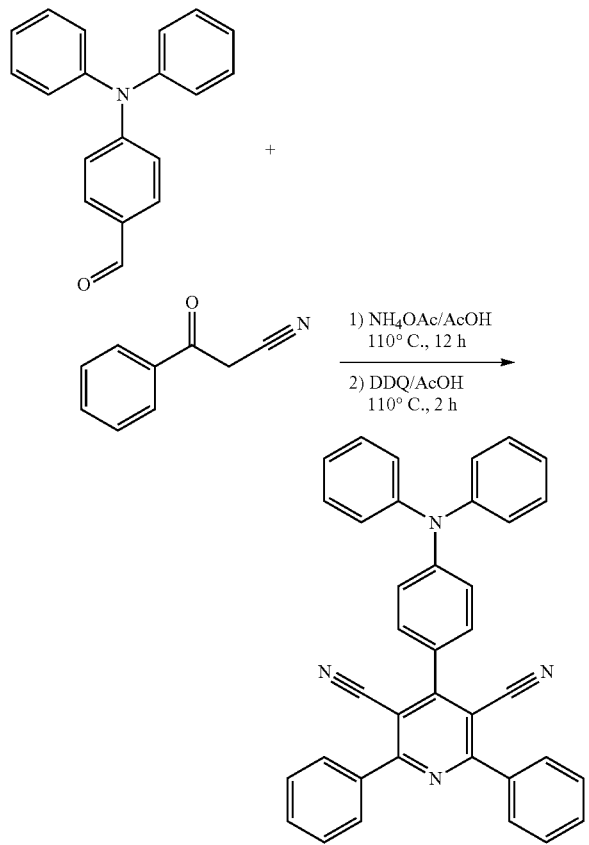

Intermediate Product I-7 (1.0 g, 3.7 mmol), benzoylacetonitrile (1.2 g, 8 mmol), and ammonium acetate (1.3 g, 16.5 mmol) were placed in a double-necked flask, acetic acid (29 mL) was added as a solvent, and the mixture was heated to 110° C. and refluxed for 12 hours. After the reaction was over and the mixture was returned to room temperature, 2,3-dichloro-5,6-dicyano-p-benzoquinone (2.5 g, 11.1 mmol) was added in the double-necked flask, acetic acid (20 mL) was added as a solvent, and the mixture was heated to 110° C., and refluxed for 2 hours for oxidation reaction. After the reaction was over and the mixture was returned to room temperature, suction filtration was performed, excess acetic acid was removed by washing with water, the solvent and water were removed by high vacuum, and a crude product was obtained. The crude product was purified by column chromatography and TPAPPC (1.5 g, total yield: 78.0%) having a yellow color was obtained as a product. Finally, the product was refined in a sublimation machine under high vacuum ($5\times10^{-6}$ torr) at a sublimation temperature of 240° C.

$^1$1-1 NMR (500 MHz, CDCl$_3$, δ): 8.03 (d, J=7.3 Hz, 6H), 7.55-7.54 (m, 2H), 7.48 (d, J=8.6 Hz, 4H), 7.32 (t, J=7.6 Hz, 4H), 7.21 (d, J=7.8 Hz, 4H), 7.13 (dd, J=13.8, 7.9 Hz, 4H). $^{13}$C NMR (125 MHz, CDCl$_3$, δ): 163.55, 155.96, 150.44, 146.52, 136.60, 131.21, 130.34, 129.64, 129.55, 128.71, 126.09, 124.91, 124.55, 120.12, 116.41, 105.57. HRMS (EI) m/z: [M+] calcd. for $C_{37}H_{24}N_4$, 524.2001; found, 524.2006. Anal. calcd. for $C_{37}H_{24}N_4$: C 84.71, H 4.61, N 10.68 found: C 84.64, H 4.43, N 10.59.

In the present embodiment, a nuclear magnetic resonance (NMR) spectrum of each compound mentioned above was measured by a spectrometer (model: Varian Mercury 500). A chemical shift in a proton nuclear magnetic resonance ($^1$H NMR) spectrum is based on CDCl$_3$ with a chemical shift set at 7.24 ppm. The symbol s represents a singlet, d represents a doublet, t represents a triplet, m represents a multiplet, dd represents a doublet of doublets, and a coupling constant is expressed in Hz. A chemical shift in a $^{13}$C NMR spectrum is based on CDCl$_3$ with a chemical shift set at 77.0 ppm. High resolution mass spectrometry (HRMS) is performed using a JEOL AccuTOF GCx high resolution gas chromatography mass spectrometer (HRGCMS) or a JEOL JMS-700 high resolution mass spectrometer (HRMS). Weight percentages of carbon, hydrogen, nitrogen and sulfur in a sample were measured by an elemental analyzer which is a fully automatic elemental analyzer (model: vario EL III CHN-OS Rapid, made by Elementar).

Evaluation of Properties of Compound

Photophysical Properties

Analysis of Ultraviolet-visible (UV-vis) Absorption Spectra and Photoluminescence Spectra The compounds of Synthesis Examples 8 to 13 and Synthesis Comparative Example 1 were placed in $10^{-5}$ M toluene solution, calibrated in a quartz sample tank, measured by a spectrophotometer (model: Hitachi U-3300) for UV-vis absorption spectra, and measured by a fluorescence spectrophotometer (model: Hitachi F-7000) for photoluminescence (PL) spectra.

Analysis of Ultraviolet Photoelectron Spectra

In the present embodiment, the compounds of Synthesis Examples 8 to 13 and Synthesis Comparative Example 1 were measured by a photoelectron spectrometer for electron detachment energy in a film state, so as to obtain ultraviolet photoelectron spectra. Specifically, each sample was formed into an undoped film and disposed on a glass substrate, and a surface of the film was irradiated with ultraviolet light. Since valence electrons on a compound surface have a relatively small attractive force with respect to the nucleus, the valence electrons are emitted from the surface after absorbing high energy, form negatively charged $O_2^-$ with oxygen, and enter a detector under acceleration by an electric field. The initial energy of the electrons detected by the detector is a HOMO energy level of the compound, expressed in electron volts (eV). An energy gap ($E_g$) from the ground state to the singlet excited state is calculated using an onset of an absorption spectrum, and a LUMO energy level of the compound is then calculated from the HOMO energy level and $E_g$.

Figure 4:
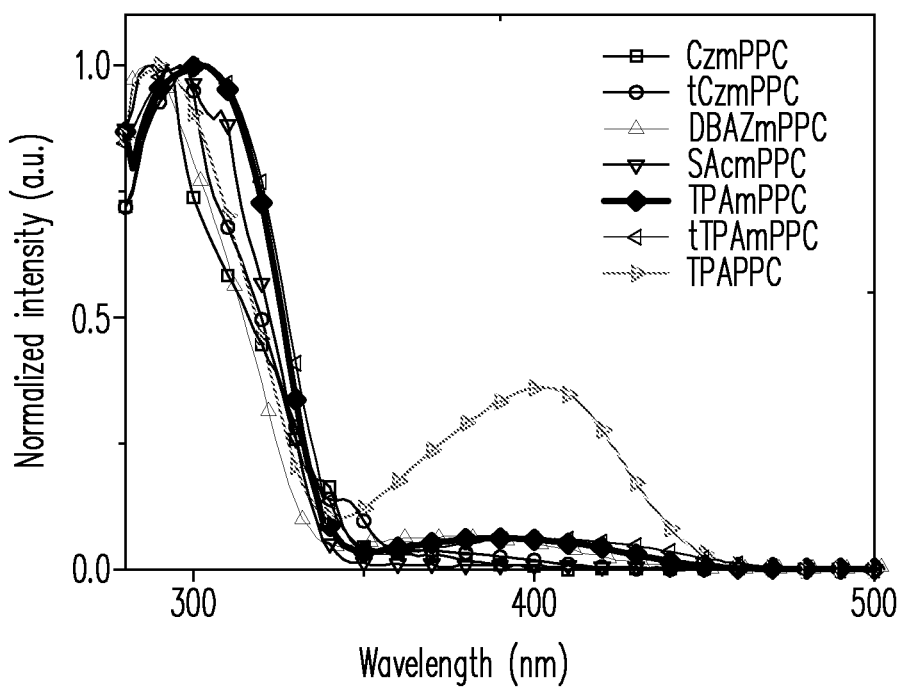
FIG. 4 shows ultraviolet-visible (UV-vis) absorption spectra of compounds of Synthesis Examples 8 to 13 and Synthesis Comparative Example 1.
Figure 5:
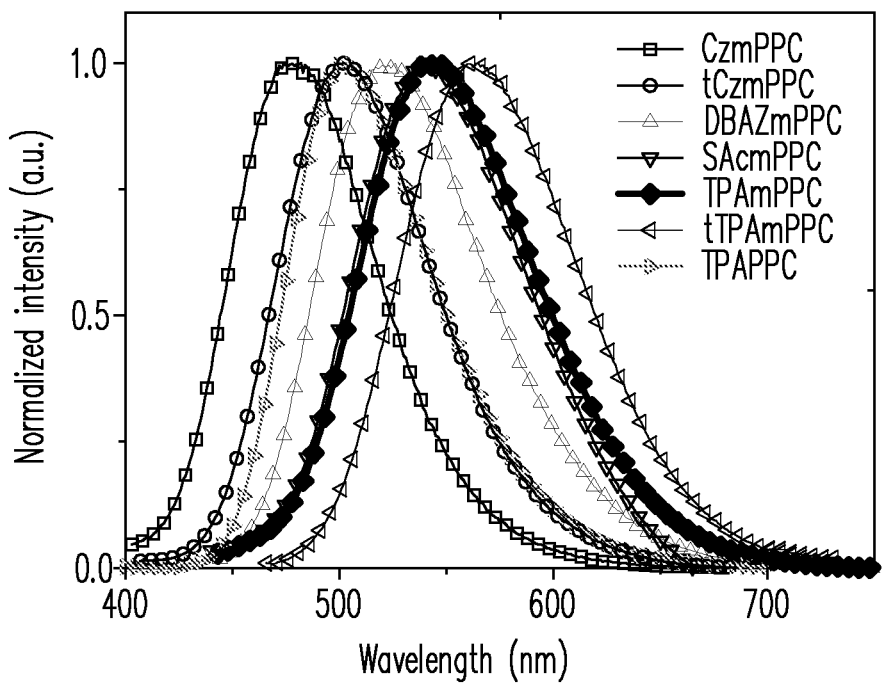
FIG. 5 shows photoluminescence spectra of the compounds of Synthesis Examples 8 to 13 and Synthesis Comparative Example 1.

Results of the UV-vis absorption spectra, the photoluminescence spectra, and the ultraviolet photoelectron spectra of the compounds of Synthesis Examples 8 to 13 and Synthesis Comparative Example 1 are shown in Table 3 below. FIG. 4 shows the UV-vis absorption spectra of the compounds of Synthesis Examples 8 to 13 and Synthesis Comparative Example 1. FIG. 5 shows the photoluminescence spectra of the compounds of Synthesis Examples 8 to 13 and Synthesis Comparative Example 1.

TABLE 3

|  | $\lambda_{abs}$ (nm) | $\lambda_{Tol}$ (nm) | $E_g$ (eV) | HOMO (eV) | LUMO (eV) |
|---|---|---|---|---|---|
| Synthesis Example |  |  |  |  |  |
| CzmPPC | 292 | 482 | 3.07 | −5.82 | −2.75 |
| tCzmPPC | 298 | 502 | 2.92 | −5.72 | −2.80 |
| DBAZmPPC | 288 | 526 | 2.73 | −5.72 | −2.99 |
| SAcmPPC | 296 | 534 | 2.68 | −5.61 | −2.93 |
| TPAmPPC | 302 | 544 | 2.61 | −5.69 | −3.08 |
| tTPAmPPC | 304 | 564 | 2.53 | −5.60 | −3.07 |
| Synthesis Comparative Example |  |  |  |  |  |
| TPAPPC | 290 | 503 | 2.64 | −5.76 | −3.12 |

$\lambda_{abs}$: absorption wavelength in toluene $\lambda_{Tol}$: emission wavelength in toluene As can be seen from Table 3 and FIG. 4 to FIG. 5, the pyridine-carbonitrile compound of the disclosure has a HOMO energy level of −5.82 eV to −5.60 eV, and a LUMO energy level of −3.12 eV to −2.75 eV. In addition, the pyridine-carbonitrile compound of the disclosure emits light ranging from sky blue light, green light to yellow light, and has an emission wavelength of 482 nm to 564 nm. That is, depending on the nitrogen-containing group ($R_3$) in the para position on the phenyl group, the pyridine-carbonitrile compound of the disclosure varies in emission color. That is, the pyridine-carbonitrile compound of the disclosure is capable of emitting light of different colors. Therefore, in the disclosure, the emission color of the pyridine-carbonitrile compound can be controlled by changing the structure of the nitrogen-containing group ($R_3$) of the pyridine-carbonitrile compound.

Analysis of Room Temperature Fluorescence Spectra and Low Temperature Phosphorescence Spectra The compounds of Synthesis Examples 8 to 13 and Synthesis Comparative Example 1 were each doped at 10 wt % into a host light-emitting material mCPCN, evaporated on a quartz plate to a thickness of 30 nm to form a film, and the film was placed in a transparent quartz tube. Room temperature fluorescence spectra and low temperature phosphorescence spectra were measured using a fluorescence spectrophotometer (model: Hitachi F-7000). In the present embodiment, a measurement temperature of the room temperature fluorescence spectra was 298 K, and a measurement temperature of the low temperature phosphorescence spectra was 77 K. $E_S$ was calculated using an initial wavelength of the fluorescence spectra, $E_T$ was calculated using an initial wavelength of the phosphorescence spectra, and $\Delta E_{ST}$ was obtained by subtracting $E_T$ from $E_S$ and is expressed in electron volts (eV). Results of the room temperature fluorescence spectra and the low temperature phosphorescence spectra are shown in Table 4 below.

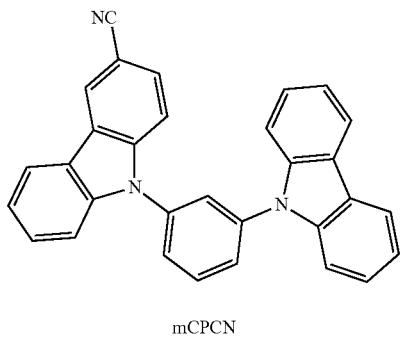 [SMILES: N#Cc1ccc2c(c1)c1ccccc1n2-c1cccc(-n2c3ccccc3c3ccccc32)c1]

mCPCN

Measurement of Photoluminescence Quantum Yield

The compounds of Synthesis Examples 8 to 13 and Synthesis Comparative Example 1 were each doped at 10 wt % into the host light-emitting material mCPCN, and evaporated on a quartz plate to a thickness of 30 nm to form a film. Calibration was performed with a blank quartz plate. Then, the photoluminescence quantum yield (PLQY) of the film sample on the quartz plate was measured using an integrating sphere under nitrogen.

TABLE 4

|  | $E_S$ (eV) | $E_T$ (eV) | $\Delta E_{ST}$ (eV) | $\Phi_{PLQY}$ (%) |
|---|---|---|---|---|
| Synthesis Example |  |  |  |  |
| CzmPPC | 2.95 | 2.68 | 0.27 | 92 |
| tCzmPPC | 2.82 | 2.70 | 0.12 | 97 |
| DBAZmPPC | 2.80 | 2.78 | 0.02 | 24 |
| SAcmPPC | 2.73 | 2.68 | 0.05 | 100 |
| TPAmPPC | 2.69 | 2.67 | 0.02 | 100 |
| tTPAmPPC | 2.60 | 2.58 | 0.02 | 79 |
| Synthesis Comparative Example |  |  |  |  |
| TPAPPC | 2.73 | 2.52 | 0.21 | 100 |

Figure 6:
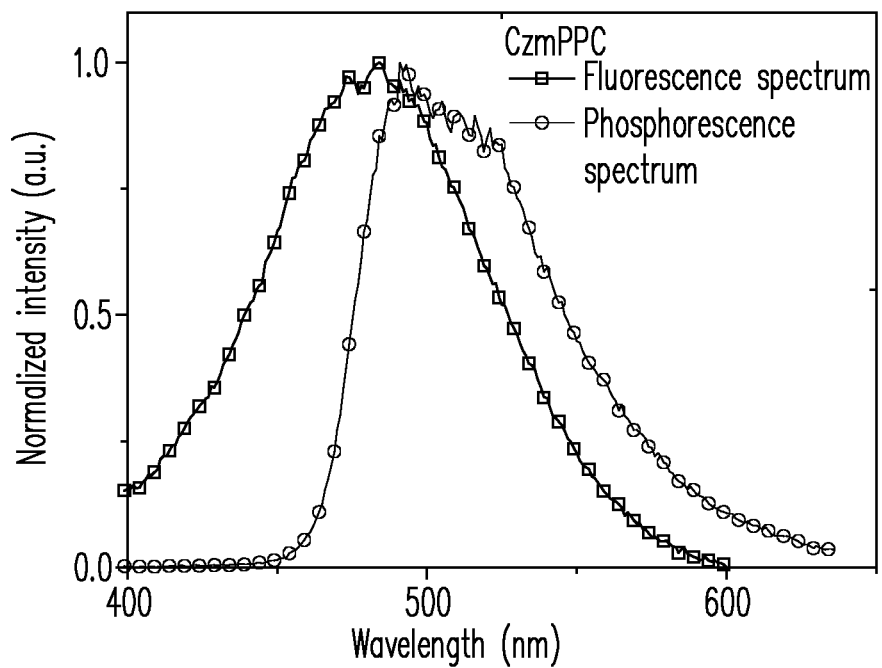
FIG. 6 shows a room temperature fluorescence spectrum and a low temperature phosphorescence spectrum of CzmPPC according to an embodiment of the disclosure.
Figure 7:
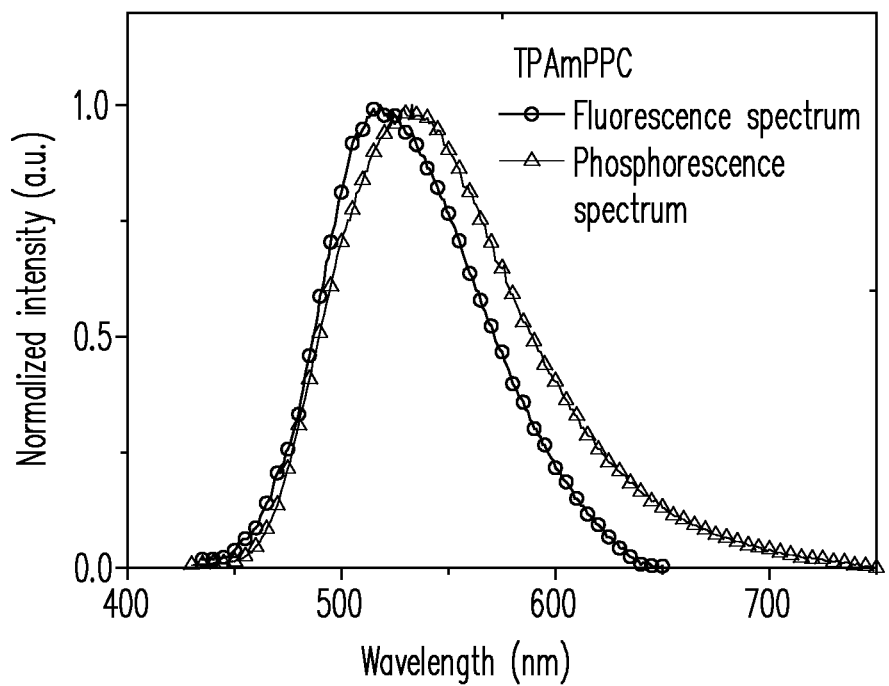
FIG. 7 shows a room temperature fluorescence spectrum and a low temperature phosphorescence spectrum of TPAmPPC according to an embodiment of the disclosure.
Figure 8:
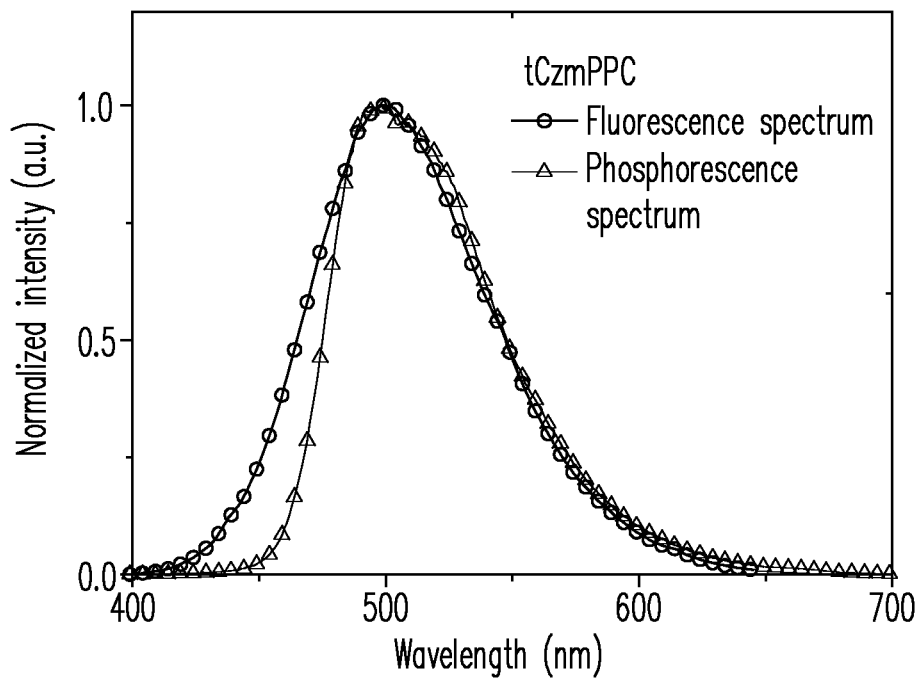
FIG. 8 shows a room temperature fluorescence spectrum and a low temperature phosphorescence spectrum of tCzmPPC according to an embodiment of the disclosure.
Figure 9:
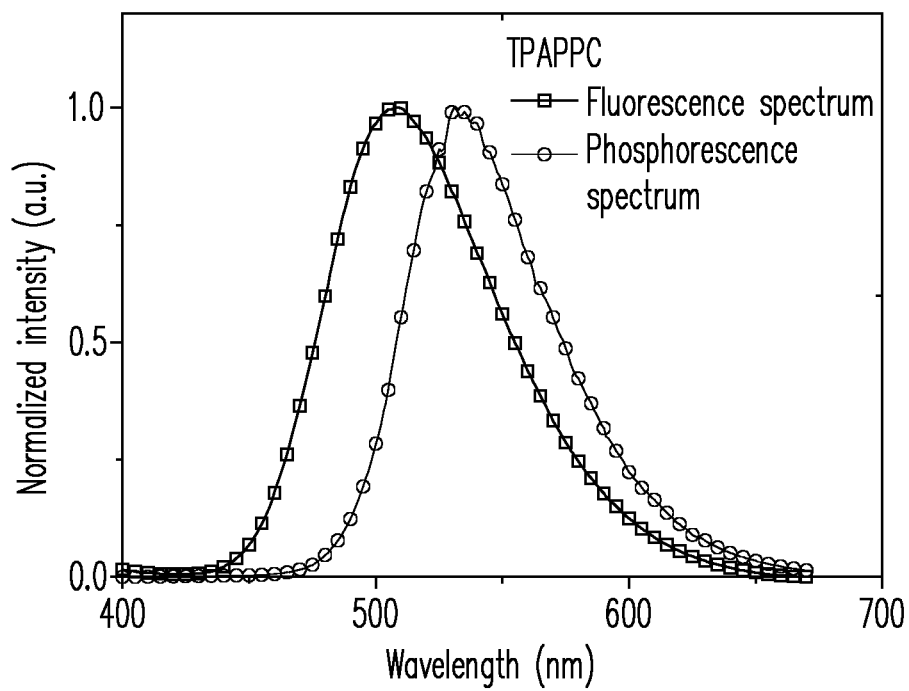
FIG. 9 shows a room temperature fluorescence spectrum and a low temperature phosphorescence spectrum of TPAPPC according to an embodiment of the disclosure.

FIG. 6 shows a room temperature fluorescence spectrum and a low temperature phosphorescence spectrum of CzmPPC according to an embodiment of the disclosure. FIG. 7 shows a room temperature fluorescence spectrum and a low temperature phosphorescence spectrum of TPAmPPC according to an embodiment of the disclosure. FIG. 8 shows a room temperature fluorescence spectrum and a low temperature phosphorescence spectrum of tCzmPPC according to an embodiment of the disclosure. FIG. 9 shows a room temperature fluorescence spectrum and a low temperature phosphorescence spectrum of TPAPPC according to an embodiment of the disclosure.

As shown in FIG. 6 to FIG. 9 and Table 4, $\Delta E_{ST}$ of the pyridine-carbonitrile compound of the disclosure ranges from 0.02 eV to 0.27 eV, which is consistent with the characteristic ($\Delta E_{ST}$<0.3 eV) of thermally activated delayed fluorescent molecules. The smaller the $\Delta E_{ST}$, the more likely the molecules are to return from the triplet excited state to the singlet excited state and emit delayed fluorescence.

In addition, as shown in Table 4, the PLQYs of the pyridine-carbonitrile compounds CzmPPC, tCzmPPC, TPAmPPC, SAcmPPC, and tTPAmPPC of the disclosure in the film form were respectively 92%, 97%, 100%, 100%, and 79%, and the performance of these pyridine-carbonitrile compounds in the film form have fulfilled expectations. Since pyridine-3,5-dicarbonitrile has good rigidity in molecular structure, and steric hindrance between the dimethyl group on the phenyl group (linking group) and the dicyano group on the pyridine suppresses non-radiative decay such as molecular motion, the pyridine-carbonitrile compound may attain a PLQY close to 100%. This shows that the pyridine-carbonitrile compound of the disclosure has the potential to become a high-efficiency TADF material and is favorable for application in a light-emitting element.

Thermal Stability Test

In an evaporation process for manufacturing an OLED device, it is necessary to ensure that a compound does not decompose at high temperatures and that an amorphous film can be formed so that charge transfer will not be hindered by crystals. In addition, during operation of the device, excitons are exposed to a charged environment. Therefore, the compound must have a high bond dissociation energy (BDE).

In the present embodiment, a change in material weight relative to temperature was measured using a thermogravimetric analyzer (TGA) (made by Mettler Toledo) at a heating rate of 10° C./min under nitrogen, thereby obtaining decomposition temperature ($T_d$) of the compounds of Synthesis Examples 8 to 13 and Synthesis Comparative Example 1. The decomposition temperature is defined as the temperature at which 5% of the weight is lost. The decomposition temperatures of the compounds of Synthesis Examples 8 to 13 and Synthesis Comparative Example 1 are shown in Table 5 below.

Delayed Fluorescence Characteristics Test

The compounds of Synthesis Examples 8 to 13 and Synthesis Comparative Example 1 were each doped at 10 wt % into the host light-emitting material mCPCN, evaporated on a quartz plate, and measured by a transient photoluminescence spectrometer (model: Edinburgh FLS980-S2S2-stm) for transient photoluminescence (PL) spectra. Moreover, prompt fluorescence lifetime ($\tau_p$), delayed fluorescence lifetime ($\tau_d$), prompt fluorescence quantum efficiency ($\Phi_{prompt}$) and delayed fluorescence quantum efficiency ($\Phi_{delayed}$) were calculated using the F980 software, and the results are shown in Table 5 below.

TABLE 5

|  | $T_d$ (° C.) | $\tau_p$ (ns) | $\tau_d$ (μs) | $\Phi_{prompt}$ (%) | $\Phi_{delayed}$ (%) |
|---|---|---|---|---|---|
| Synthesis Example |  |  |  |  |  |
| CzmPPC | 363 | 42 | 462 | 19 | 73 |
| tCzmPPC | 374 | 54 | 87 | 25 | 72 |
| DBAZmPPC | 371 | 15 | 0.1 | 5 | 19 |
| SAcmPPC | 400 | 99 | 72 | 16 | 84 |
| TPAmPPC | 336 | 33 | 3 | 9 | 91 |
| tTPAmPPC | 370 | 14 | 2 | 3 | 76 |
| Synthesis Comparative Example |  |  |  |  |  |
| TPAPPC | 380 | 10 | 134 | 5 | 95 |

As can be seen from Table 5, the pyridine-carbonitrile compound of the disclosure has a decomposition temperature of 336° C. to 400° C., and exhibits good thermal stability. Therefore, it can be ensured that no decomposition occurs during the evaporation process.

In addition, the pyridine-carbonitrile compound of the disclosure has a prompt fluorescence lifetime ($\tau p$) of less than 100 nanoseconds (ns). This is expressed by prompt emission of light during a return to the ground state from the singlet excited state, and indicates that TADF characteristics have been achieved. The pyridine-carbonitrile compound of the disclosure has a short delayed fluorescence lifetime ($\tau d$), a high delayed fluorescence quantum efficiency ($\Phi_{delayed}$), and excellent TADF characteristics. In contrast, in TPAPPC of the synthetic comparative example, due to the lack of steric hindrance at the ortho position of the phenyl group, the electron clouds of the HOMO and LUMO partially overlapped, and relatively large $\Delta E_{ST}$ was obtained. As a result, TPAPPC had a relatively long delayed fluorescence lifetime (134 microseconds (μs)).

Fabrication of Organic Light-Emitting Diode

Experiment Example 1

An organic light-emitting diode (OLED) was fabricated using 9-(3-(9H-carbazol-9-yl)phenyl)-9H-carbazole-3-carbonitrile (mCPCN) as a host light-emitting material, and the compound CzmPPC obtained in Synthesis Example 8 as a guest light-emitting material (i.e., dopant).

A fabrication process of the OLED was as follows. First, molybdenum trioxide ($MoO_3$) was deposited on an ITO glass substrate serving as an anode, to form a hole injection layer. Next, 1,1-bis[4-[N,N'-di(p-tolyl)amino]phenyl] cyclohexane (TAPC) was deposited on the hole injection layer to form a hole transport layer. Then, 1,3-bis(9-carbazolyl) benzene (mCP) was deposited on the hole transport layer to form an exciton blocking layer. Next, the host light-emitting material mCPCN (20 nm) doped with 10% of the compound CzmPPC was deposited to form a light-emitting layer. Then, 3,3',3"-[borylidynetris(2,4,6-trimethyl-3,1-phenylene)]tris [pyridine] (3 TPYMB) (50 nm) was deposited on the light-emitting layer to form an electron transport layer. After that, LiF (electron injection layer) (0.5 nm) and Al were sequentially deposited on the electron transport layer to form a cathode. At this point, the fabrication of the OLED of the present Experimental Example was completed. In the present embodiment, the pyridine-carbonitrile compound CzmPPC of the disclosure was used as a dopant.

The aforementioned OLED had the following structure: ITO/$MoO_3$ (1 nm)/TAPC (50 nm)/mCP (10 nm)/mCPCN: CzmPPC (10 wt %) (20 nm)/3TPYMB (50 nm)/LiF (0.5 nm)/Al (100 nm).

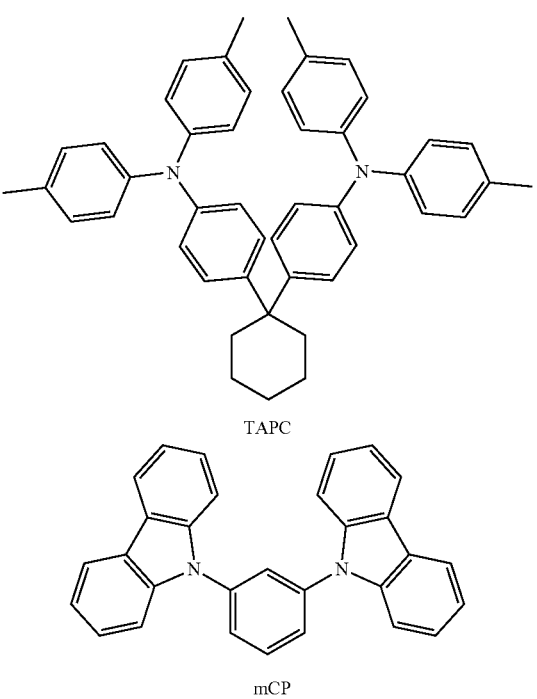

TAPC mCP

-continued

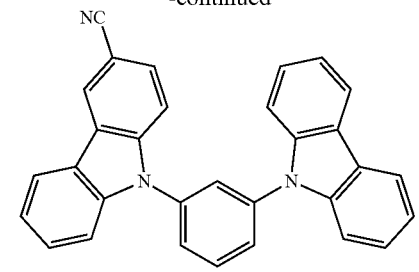

mCPCN

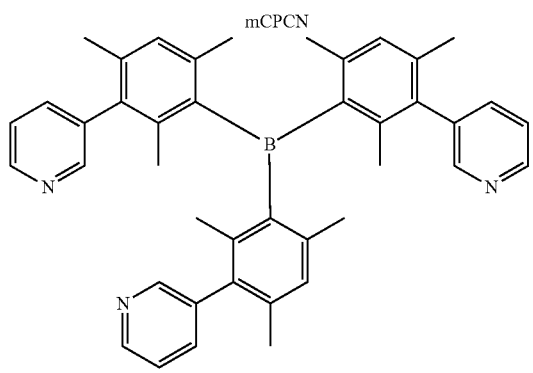

3TPYMB

Experiment Example 2

An OLED was fabricated similarly to Experimental Example 1, except that the compound tCzmPPC obtained in Synthesis Example 9 was used as the dopant of the light-emitting layer.

Experiment Example 3

An OLED was fabricated similarly to Experimental Example 1, except that the compound DBAZmPPC obtained in Synthesis Example 10 was used as the dopant of the light-emitting layer.

Experiment Example 4

An OLED was fabricated similarly to Experimental Example 1, except that the compound SAcmPPC obtained in Synthesis Example 11 was used as the dopant of the light-emitting layer.

Experiment Example 5

An OLED was fabricated similarly to Experimental Example 1, except that the compound TPAmPPC obtained in Synthesis Example 12 was used as the dopant of the light-emitting layer.

Experiment Example 6

An OLED was fabricated similarly to Experimental Example 1, except that the compound tTPAmPPC obtained in Synthesis Example 13 was used as the dopant of the light-emitting layer.

Comparative Example 1

An OLED was fabricated similarly to Experimental Example 1, except that the compound TPAPPC obtained in Synthesis Comparative Example 1 was used as the dopant of the light-emitting layer.

Comparative Example 2

An OLED was fabricated similarly to Experimental Example 1, except that the compound TPAsPPC was used as the dopant of the light-emitting layer.

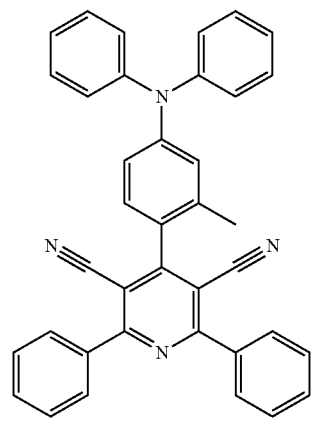

TPAsPPC

Comparative Example 3

An OLED was fabricated similarly to Experimental Example 1, except that the compound tCzmPMC was used as the dopant of the light-emitting layer. In the structure of the compound tCzmPMC, a methyl group was introduced into positions 2 and 6 ($R_3$) of the pyridyl group as the core structure.

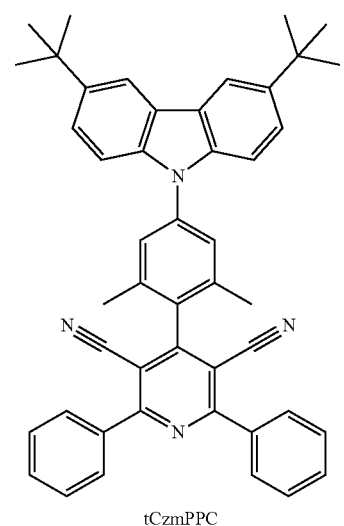 [SMILES: Cc1cc(-n2c3ccc(C(C)(C)C)cc3c3cc(C(C)(C)C)ccc32)cc(C)c1-c1c(C#N)c(-c2ccccc2)nc(-c2ccccc2)c1C#N ; "tCzmPPC"]

tCzmPPC

Performance Evaluation of Organic Light-Emitting Diode

Figure 10:
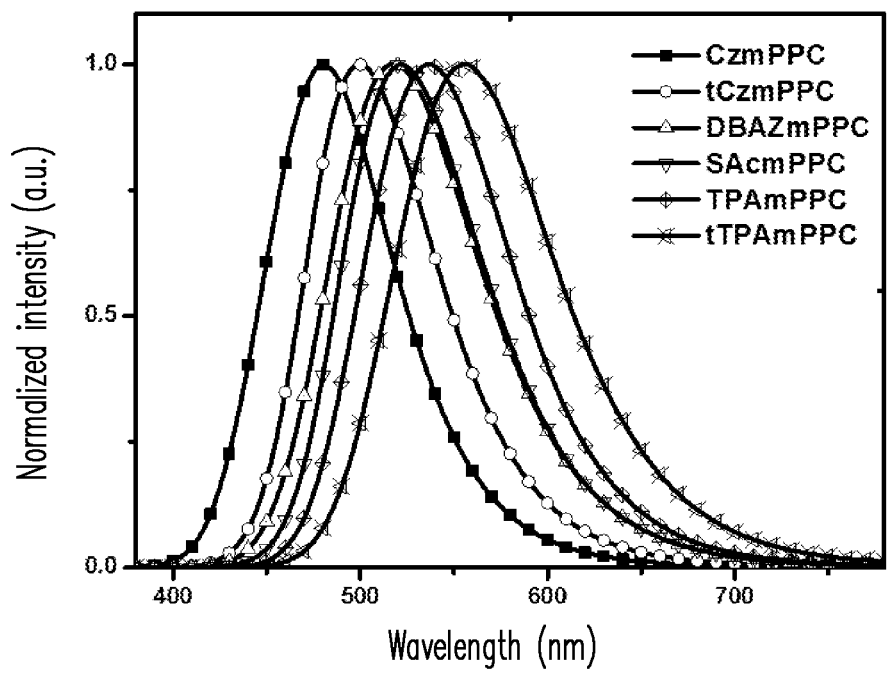
FIG. 10 shows photoluminescence spectra of organic light-emitting diodes (OLEDs) of Experimental Examples 1 to 6.

FIG. 10 shows photoluminescence spectra of the OLEDs of Experimental Examples 1 to 6. Table 6 shows results of testing the performance of the OLEDs of Experimental Examples 1 to 6 and Comparative Examples 1 to 3. In the present embodiment, a threshold voltage of an OLED is an operating voltage when the luminance of the element is 1 cd m$^{-2}$. The luminance, external quantum efficiency, luminous efficiency, and power efficiency of the OLED are respectively the maximum values of the element. The emission wavelength and CIE coordinates of the OLED are electroluminescence characteristics at an operating voltage of 8 V.

Among the aforementioned experimental examples, the OLED (with the compound SAcmPPC as the dopant) of Experimental Example 4 and the OLED (with the compound TPAmPPC as the dopant) of Experimental Example 5 exhibited excellent element efficiency: their respective maximum external quantum efficiencies were 37.6% and 39.8%, their respective maximum luminous efficiencies were 122.8 cd A$^{-1}$ and 133.5 cd A$^{-1}$, and their respective maximum power efficiencies were 128.6 lm W$^{-1}$ and 139.8 lm W$^{-1}$, showing

TABLE 6

| | Dopant | Threshold voltage (V) | Luminance (cd m$^{-2}$) | External quantum efficiency (%) | Luminous efficiency (cd A$^{-1}$) | Power efficiency (lm W$^{-1}$) | Emission wavelength (nm) | CIE coordinates |
|---|---|---|---|---|---|---|---|---|
| Experiment Example 1 | CzmPPC | 3.0 | 581 | 16.1 | 36.8 | 38.5 | 480 | (0.16, 0.27) |
| Experiment Example 2 | tCzmPPC | 2.8 | 3906 | 28.0 | 76.4 | 106.7 | 499 | (0.21, 0.45) |
| Experiment Example 3 | DBAZmPPC | 3.0 | 2011 | 14.6 | 47.2 | 49.4 | 518 | (0.28, 0.53) |
| Experiment Example 4 | SAcmPPC | 2.6 | 3914 | 37.6 | 122.8 | 128.6 | 525 | (0.31, 0.56) |
| Experiment Example 5 | TPAmPPC | 2.6 | 15256 | 39.8 | 133.5 | 139.8 | 537 | (0.35, 0.57) |
| Experiment Example 6 | tTPAmPPC | 2.7 | 9872 | 29.8 | 91.8 | 96.1 | 556 | (0.42, 0.55) |
| Comparative Example 1 | TPAPPC | 2.7 | 6985 | 36.0 | 116.5 | 121.9 | 521 | (0.29, 0.56) |
| Comparative Example 2 | TPAsPPC | 2.7 | 13111 | 37.4 | 122.7 | 128.5 | 526 | (0.31, 0.56) |
| Comparative Example 3 | tCzmPMC | 3.2 | 369 | 3.2 | 4.6 | 4.2 | 450 | (0.17, 0.15) |

As can be seen from FIG. 10, the OLEDs of Experimental Examples 1 to 6 had emission wavelengths ranging from sky blue light (480 nm) to yellow light (556 nm). That is, depending on the nitrogen-containing group (R$_3$) in the para position on the phenyl group, the pyridine-carbonitrile compound of the disclosure varies in emission color. Therefore, in the disclosure, the emission color of the OLED can be controlled by changing the structure of the nitrogen-containing group (R$_3$) of the pyridine-carbonitrile compound.

In addition, as can be seen from Table 6, the threshold voltages of the OLEDs of Experimental Examples 1 to 6 were all equal to or less than 3.0 V (ranging from 2.6 V to 3.0 V). The OLED (with the compound CzmPPC as the dopant) of Experimental Example 1 had an emission wavelength of 480 nm (sky blue light), a maximum external quantum efficiency of 16.1%, a maximum luminous efficiency of 36.8 cd A$^{-1}$, and a maximum power efficiency of 38.5 lm W$^{-1}$. The OLED (with the compound tTPAmPPC as the dopant) of Experimental Example 6 had an emission wavelength of 556 nm (yellow light), a maximum external quantum efficiency of 29.8%, a maximum luminous efficiency of 91.8 cd A$^{-1}$, and a maximum power efficiency of 96.1 lm W$^{-1}$.

their superior efficiency performance compared to typical TADF materials.

Figure 11:
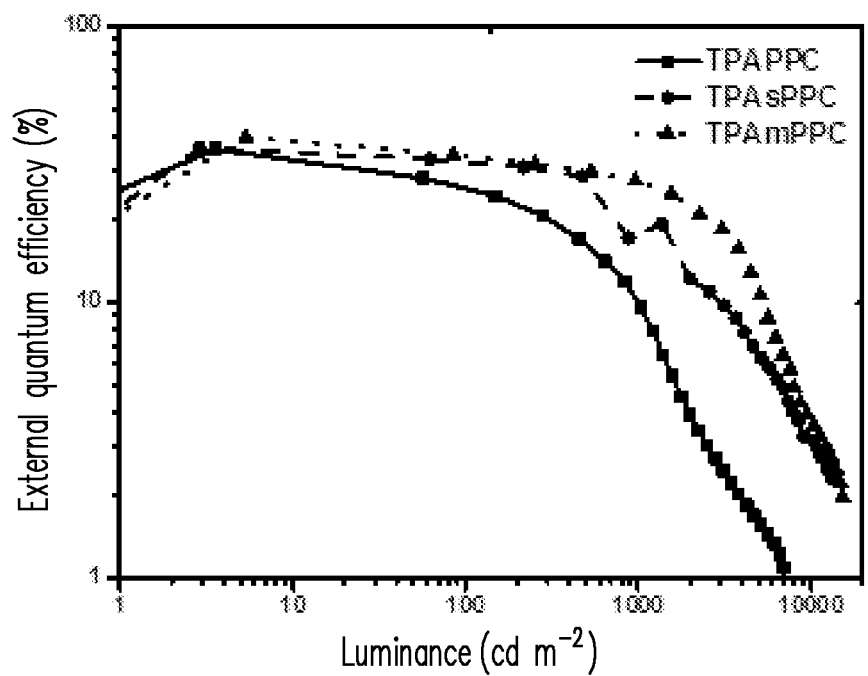
FIG. 11 shows luminance-external quantum efficiency curves of the OLEDs of Experimental Example 5, Comparative Example 1 and Comparative Example 2.

FIG. 11 shows luminance-external quantum efficiency curves of the OLEDs of Experimental Example 5, Comparative Example 1 and Comparative Example 2.

As can be seen from FIG. 11, compared with the OLED of Experimental Example 5, the OLEDs of Comparative Examples 1 and 2 showed a larger decrease in external quantum efficiency as the luminance increased. In the case of high luminance (e.g., 1000 cd m$^{-2}$), the external quantum efficiency of the OLED of Comparative Example 1 was about 9.6%, much lower than the external quantum efficiency (27.0%) of Experimental Example 5. The reason is as follows. Since the compound TPAPCC of Comparative Example 1 had relatively large $\Delta E_{ST}$, exciton-carrier quenching or exciton-exciton quenching was likely to occur at a high current density, resulting in energy and efficiency losses. That is, the above results show that the introduction of two methyl groups (which may create steric hindrance with the cyano group on the pyridyl group) into the ortho position on the phenyl group (linking group) may reduce the delayed fluorescence lifetime and improve the efficiency performance of the light-emitting element at high luminance, thereby enabling effective application in a display.

Figure 12:
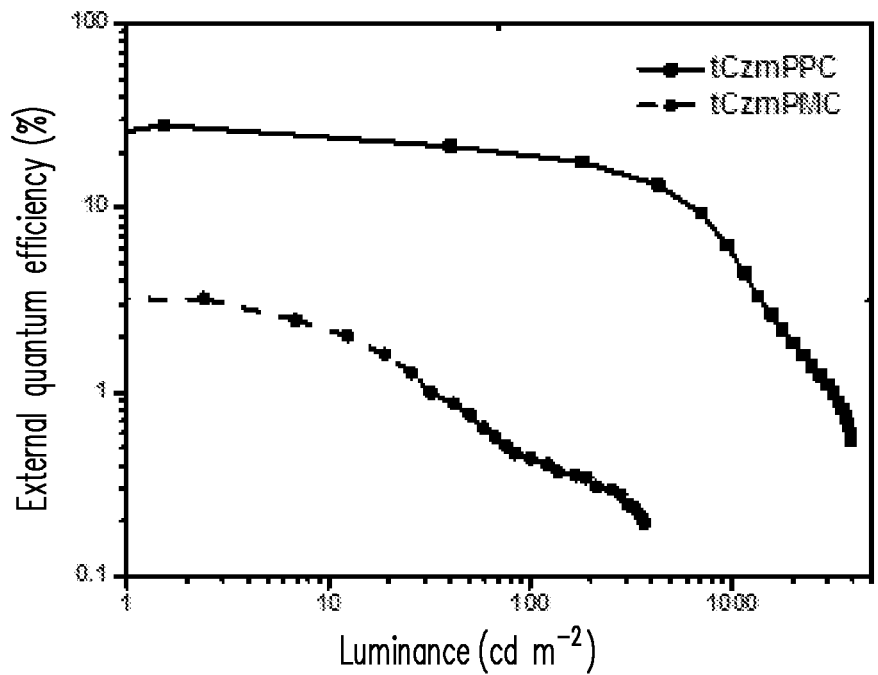
FIG. 12 shows luminance-external quantum efficiency curves of the OLEDs of Experimental Example 2 and Comparative Example 3.

FIG. 12 shows luminance-external quantum efficiency curves of the OLEDs of Experimental Example 2 and Comparative Example 3.

Referring to FIG. 12 and Table 6, the maximum external quantum efficiency, the maximum luminous efficiency and the maximum power efficiency of the OLED of Comparative Example 3 were respectively 3.2%, 4.6 cd A$^-$ and 4.2 lm W$^{-1}$, much lower than the efficiency performance of Experimental Example 2. In addition, the maximum external quantum efficiency of Comparative Example 3 was less than 5%; that is, the compound tCzmPMC of Comparative Example 3 did not exhibit a characteristic that "the utilization of excitons is improved by thermally activated delayed fluorescent molecules through conversion", and was a traditional fluorescent material. The above results show that in the pyridine-carbonitrile compound of the disclosure, the TADF characteristics and luminous efficiency are largely affected by the introduction of an aromatic group into positions 2 and 6 ($R_3$) of the pyridyl group as the core structure.

Thermal Annealing Test for Element

In the present embodiment, the thermal stability of the pyridine-carbonitrile compound of the disclosure is further tested through a thermal annealing experiment. After an OLED has undergone evaporation and has been packaged in a glove box in a nitrogen environment, the OLED is placed on a heating plate. Next, heating is performed at 50° C. and 80° C. respectively for 20 minutes, and then the OLED is allowed to stand until reaching room temperature, followed by being subjected to an electrical test.

In the present embodiment, the OLED (with the compound TPAmPPC as the dopant) of Experimental Example 5 was subjected to a thermal annealing test, and the results are shown in Table 7 below.

TABLE 7

| | Threshold voltage (V) | Luminance (cd m$^{-2}$) | External quantum efficiency (%) | Luminous efficiency (cd A$^{-1}$) | Power efficiency (lm W$^{-1}$) | CIE coordinates (x, y) |
|---|---|---|---|---|---|---|
| TPAmPPC (25° C.) | 2.6 | 15256 | 39.8 | 133.5 | 139.8 | (0.35, 0.57) |
| TPAmPPC (50° C.) | 2.6 | 15872 | 34.3 | 115.1 | 120.6 | (0.35, 0.57) |
| TPAmPPC (80° C.) | 2.6 | 14459 | 29.0 | 97.1 | 101.7 | (0.35, 0.57) |

Figure 13:
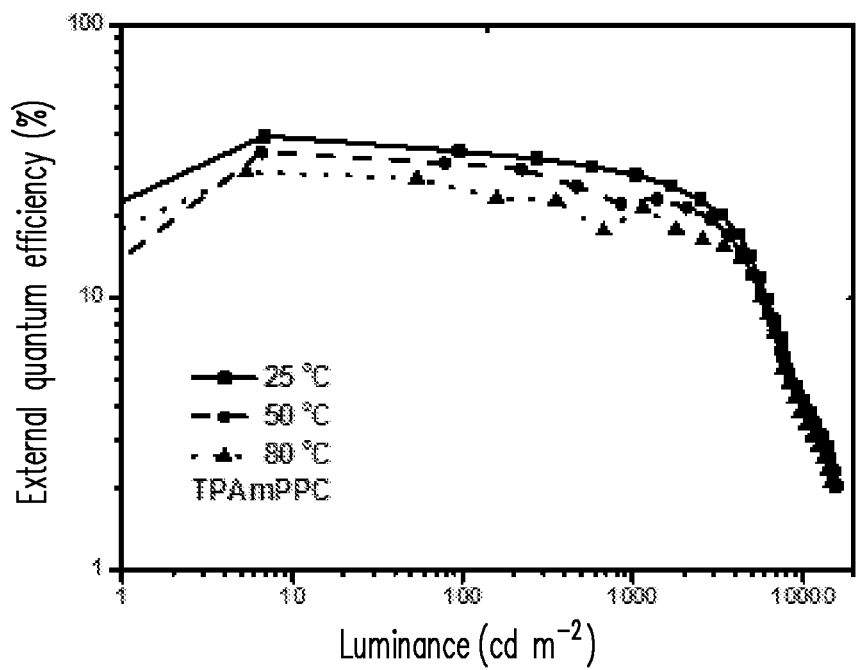
FIG. 13 shows luminance-external quantum efficiency curves of the OLED of Experimental Example 5 at different temperatures.

FIG. 13 shows luminance-external quantum efficiency curves of the OLED of Experimental Example 5 at different temperatures.

As can be seen from FIG. 13 and Table 7, even after heating at 80° C., the OLED of Experimental Example 5 still maintained thermal stability to a certain extent, and had a maximum external quantum efficiency of 29.0% and a maximum luminance of 14459 cd m$^{-2}$. In addition, light emission position and threshold voltage of the OLED of Experimental Example 5 did not change as the heating temperature was raised, and there was no light leakage in the electroluminescence spectrum. The above results show that the compound TPAmPPC exhibited good thermal stability as an organic guest light-emitting material in the OLED.

Light-Emitting Element Lifetime Test

Fabrication of Organic Light-Emitting Diode

Experiment Example 7

In the present embodiment, the materials for fabricating an OLED included: ITO as a material of the anode; 1,4,5,8,9,12-hexaazatriphenylenehexacarbonitrile (HAT-CN) as a material of the hole injection layer; 9-Phenyl-3,6-bis(9-phenyl-9Hcarbazol-3-yl)-9H-carbazole (Tris-PCz) as a material of the hole transport layer; 1,3-bis(9-carbazolyl)benzene (mCP) as a material of the exciton blocking layer, 3,3'-Di(9H-carbazol-9-yl)-1,1'-biphenyl (mCBP) as a host material in the light-emitting layer; the pyridine-carbonitrile compound CzmPPC of the disclosure as a guest material in the light-emitting layer, 2,4,6-tris(biphenyl-3-yl)-1,3,5-triazine (T2T) as a material of the hole blocking layer, 2,7-bis(2,2'-bipyridin-5-yl)triphenylene (BPy-TP2) as a material of the electron transport layer, LiF as a material of the electron injection layer, and Al as a material of the cathode.

The aforementioned OLED had the following structure: iTO/HAT-CN (10 nm)/Tris-PCz (30 nm)/mCP (10 nm)/mCBP: 10 wt % guest material (30 nm)/T2T (10 nm)/BPy-TP2 (40 nm)/LiF (1.0 nm)/Al (100 nm).

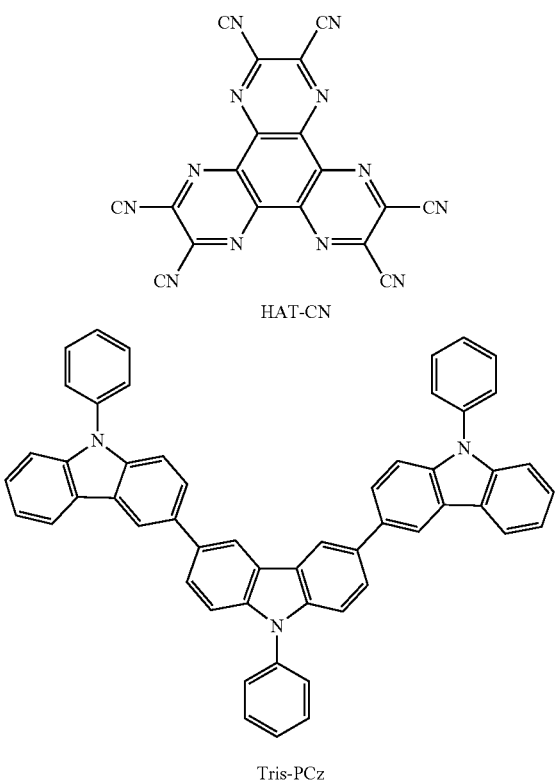

T2T mCBP

BPy-TP2 mCP

Experiment Example 8

An OLED was fabricated similarly to Experimental Example 7, except that the compound tCzmPPC obtained in Synthesis Example 9 was used as the dopant of the light-emitting layer.

Experiment Example 9

An OLED was fabricated similarly to Experimental Example 7, except that the compound SAcmPPC obtained in Synthesis Example 11 was used as the dopant of the light-emitting layer.

Experiment Example 10

An OLED was fabricated similarly to Experimental Example 7, except that the compound TPAmPPC obtained in Synthesis Example 12 was used as the dopant of the light-emitting layer.

Experiment Example 11

An OLED was fabricated similarly to Experimental Example 7, except that the compound tTPAmPPC obtained in Synthesis Example 13 was used as the dopant of the light-emitting layer.

Comparative Example 4

An OLED was fabricated similarly to Experimental Example 7, except that the compound TPAPPC obtained in Synthesis Comparative Example 1 was used as the dopant of the light-emitting layer.

Figure 14:
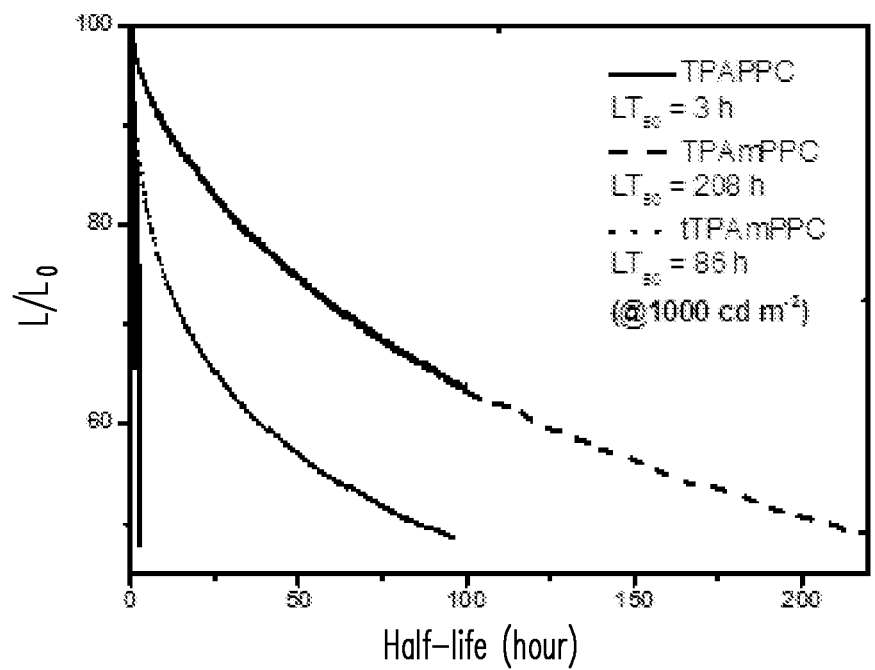
FIG. 14 shows results of a light-emitting element lifetime test conducted on Experimental Example 10, Experimental Example 11, and Comparative Example 4.

A method for testing half-life of an element is to measure the time taken for the luminance of the OLED to decay from 1000 cd m$^{-2}$ as the initial luminance ($L_0$=1000 cd m$^{-2}$) to half (L=500 cd m$^{-2}$). Measurement results are shown in Table 8 below. FIG. 14 shows results of a light-emitting element lifetime test conducted on Experimental Example 10, Experimental Example 11, and Comparative Example 4.

TABLE 8

| | Dopant | Threshold voltage (V) | Luminance (cd m$^{-2}$) | External quantum efficiency (%) | Luminous efficiency (cd A$^{-1}$) | Power efficiency (lm W$^{-1}$) | Emission wavelength (nm) | Element half-life (hr) |
|---|---|---|---|---|---|---|---|---|
| Experiment Example 7 | CzmPPC | 3.6 | 4178 | 8.5 | 24.6 | 19.3 | 504 | 2 |

As can be seen from FIG. 14 and Table 8, the OLED (with the compound TPAmPPC as the dopant) of Experimental Example 10 had the longest half-life of 208 hours, which was significantly longer than the half-life (3 hours) of the OLED (with the compound TPAPPC as the dopant) of Comparative Example 4. The reason is as follows. Since the compound TPAmPPC had a relatively short delayed fluorescence lifetime, the time during which the material was in an excited state was reduced and reaction with holes, electrons and excitons in the environment was avoided, thereby avoiding the occurrence of non-radiative decay paths or chemical bond cleavage, and greatly improving the stability of the light-emitting element.

The pyridine-carbonitrile compound of the disclosure, as a guest material of an OLED element, has excellent TADF characteristics and molecular rigidity. In the pyridine-carbonitrile compound, by changing the electron donating group in the para position of the phenyl group and introducing the dimethyl group into the ortho position of the phenyl group, the delayed fluorescence lifetime can be reduced, fast reverse intersystem crossing (RISC) and 100% luminous quantum efficiency can be achieved, thereby enabling effective use of excitons. In addition, an electroluminescent element made by the aforementioned pyridine-carbonitrile compound may have an element efficiency of nearly 40% and a maximum luminance of 15256 cd m$^{-2}$, and may maintain an external quantum efficiency of 27.0% even under high luminance (e.g., 1000 cd m$^{-2}$), which satisfies the specifications required for practical applications.

In addition, the thermal annealing test and the lifetime test show that the pyridine-carbonitrile compound of the disclosure has good stability and satisfies the need for long-term operation of panels.

Although the disclosure has been described with reference to embodiments thereof, it will be apparent to one of ordinary skill in the art that modifications and variations may be made without departing from the spirit of the disclosure. Accordingly, the scope of the disclosure will be defined by the attached claims.

What is claimed is:

1. A pyridine-carbonitrile compound represented by Chemical Formula 1:

(Chemical formula 1)

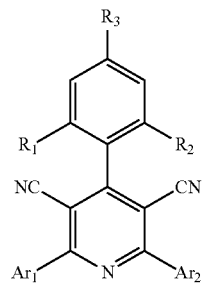

wherein Ar$_1$ and Ar$_2$ are the same or different and are each independently a substituted or unsubstituted aryl group, or a substituted or unsubstituted heteroaryl group;

R$_1$ and R$_2$ are the same or different and are each independently a substituted or unsubstituted alkyl group; and R3 is a nitrogen-containing group, wherein R3 is one selected from the following structures:

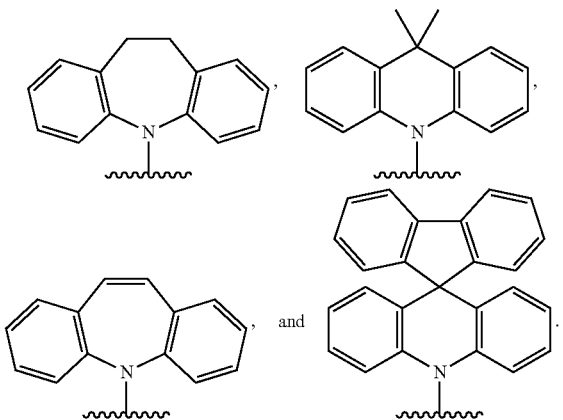

2. The pyridine-carbonitrile compound according to claim 1, wherein Ar$_1$ and Ar$_2$ are each independently one selected from the following structures:

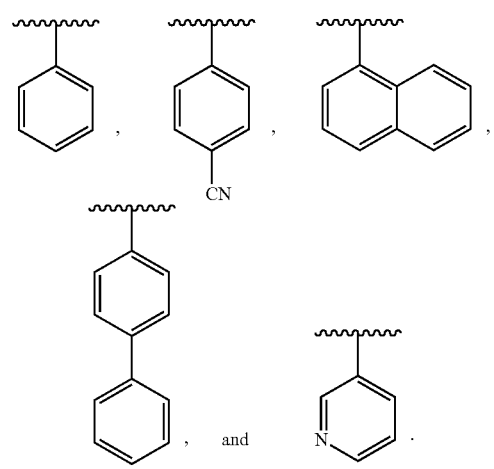

3. The pyridine-carbonitrile compound according to claim 1, wherein R$_1$ and R$_2$ are each independently a methyl group, an ethyl group or a propyl group.

4. The pyridine-carbonitrile compound according to claim 1, represented by one of the following structural formulas:

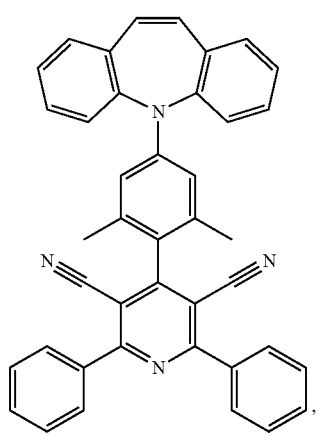 [SMILES: Cc1cc(N2c3ccccc3CCc3ccccc32)cc(C)c1-c1c(C#N)c(-c2ccccc2)nc(-c2ccccc2)c1C#N]

-continued

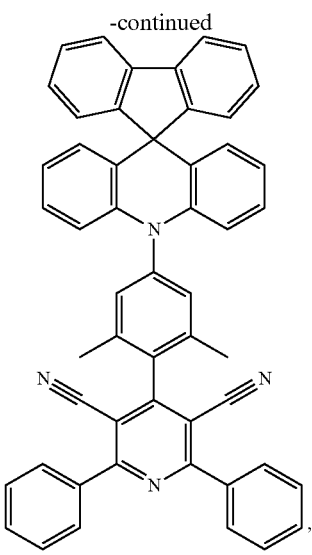

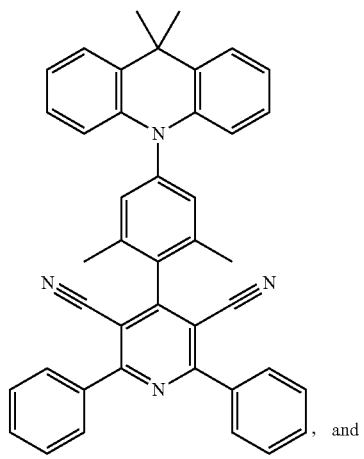
, and

-continued

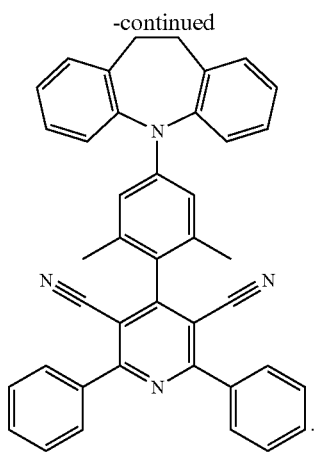
.

5. An electroluminescent device comprising:
   a cathode;
   an anode; and
   a light-emitting layer, disposed between the cathode and the anode, wherein the light-emitting layer comprises the pyridine-carbonitrile compound according to claim 1.

6. The electroluminescent device according to claim 5, wherein the light-emitting layer comprises a host light-emitting material and a guest light-emitting material.

7. The electroluminescent device according to claim 6, wherein the host light-emitting material comprises the pyridine-carbonitrile compound.

8. The electroluminescent device according to claim 6, wherein the guest light-emitting material comprises the pyridine-carbonitrile compound.

9. The electroluminescent device according to claim 5, further comprising at least one auxiliary layer, wherein the auxiliary layer is selected from the group consisting of a hole injection layer, a hole transport layer, a hole blocking layer, an exciton blocking layer, an electron injection layer, an electron transport layer, and an electron blocking layer.

* * * * *